US009963512B2

(12) United States Patent
Kim et al.

(10) Patent No.: US 9,963,512 B2
(45) Date of Patent: May 8, 2018

(54) DUAL-TARGET ANTIBODY TARGETING VEGFR-2 AND DLL4, AND PHARMACEUTICAL COMPOSITION INCLUDING SAME

(71) Applicant: PharmAbcine Inc., Daejeon (KR)

(72) Inventors: Joong Kyu Kim, Daejeon (KR); Jin San Yoo, Daejeon (KR); Sang Hoon Lee, Palo Alto, CA (US); Weon Sup Lee, Daejeon (KR); Sung Woo Kim, Daejeon (KR); Sang Ryeol Shim, Daejeon (KR); Jin Sang Yoo, Daejeon (KR); Young Ae Lee, Daejeon (KR); Mi Ju Park, Daejeon (KR); Sang Soon Byun, Daejeon (KR); Hyuk Joon Lee, Daejeon (KR); Do Yun Kim, Chungcheongbuk-do (KR); Yeun Ju Kim, Daejeon (KR); Jin Hee Choi, Daejeon (KR); Kyung Hee Nahm, Daejeon (KR); Ju Ryung Nam, Daejeon (KR); Jong Geun Jeong, Daejeon (KR); Bo Young Jeong, Daejeon (KR); Eun Jin Lee, Daejeon (KR); Seon Young Lee, Seoul (KR); In Sook Park, Daejeon (KR); Jin Sook Lee, Daejeon (KR); Jae Bong Yoon, Daejeon (KR); Nam Ye Kim, Daejeon (KR); Seon Hwan Oh, Daejeon (KR)

(73) Assignee: PharmAbcine Inc., Daejeon (KR)

( * ) Notice: Subject to any disclaimer, the term of this patent is extended or adjusted under 35 U.S.C. 154(b) by 169 days.

(21) Appl. No.: 14/443,617

(22) PCT Filed: Nov. 20, 2013

(86) PCT No.: PCT/KR2013/010589
§ 371 (c)(1),
(2) Date: May 18, 2015

(87) PCT Pub. No.: WO2014/081202
PCT Pub. Date: May 30, 2014

(65) Prior Publication Data
US 2015/0315277 A1 Nov. 5, 2015

(30) Foreign Application Priority Data
Nov. 21, 2012 (KR) .................. 10-2012-0132431

(51) Int. Cl.
C07K 16/28 (2006.01)
C07K 14/705 (2006.01)
G01N 33/50 (2006.01)

(52) U.S. Cl.
CPC ........ C07K 16/2863 (2013.01); C07K 14/705 (2013.01); C07K 16/28 (2013.01); G01N 33/5023 (2013.01); C07K 2317/21 (2013.01); C07K 2317/31 (2013.01); C07K 2317/73 (2013.01); C07K 2317/76 (2013.01); C07K 2317/92 (2013.01); C07K 2319/00 (2013.01); C07K 2319/30 (2013.01); C07K 2319/32 (2013.01); G01N 2333/705 (2013.01)

(58) Field of Classification Search
CPC .. C07K 16/2863; C07K 16/28; C07K 14/705; C07K 2319/00; C07K 2319/30; C07K 2319/32; C07K 2317/31; C07K 2317/21
See application file for complete search history.

(56) References Cited

U.S. PATENT DOCUMENTS

| 2010/0260668 | A1 | 10/2010 | Ghayur et al. |
| 2012/0065380 | A1 | 3/2012 | Yoo et al. |
| 2012/0258108 | A1 | 10/2012 | Ghayur et al. |

FOREIGN PATENT DOCUMENTS

| EP | 1916001 A2 | 4/2008 |
| JP | 2010536855 A | 12/2010 |
| JP | 2012500621 A | 1/2012 |
| JP | 2012525149 A | 10/2012 |
| JP | 2012527234 A | 11/2012 |
| WO | 03031475 A2 | 4/2003 |
| WO | 2008153237 A1 | 12/2008 |
| WO | 2009025867 A2 | 2/2009 |
| WO | 2009149185 A2 | 12/2009 |
| WO | 2010129304 A2 | 11/2010 |

OTHER PUBLICATIONS

Demarest, S., et al., "Emerging Antibody Combinations in Oncology", "mAbs", Jul. 1, 2011, pp. 338-351, vol. 3, No. 4.
Funahashi, Y., et al., "A Notch1 Ectodomain Construct Inhibits Endothelial Notch Signaling, Tumor Growth, and Angiogenesis", Cancer Research, Jun. 15, 2008, pp. 4727-4735, vol. 68.
Kuhnert, F., et al., "Dll4-Notch signaling as a therapeutic target in tumor angiogenesis", Vascular Cell, Sep. 18, 2011, p. 20 (1-8), vol. 3.
Lee, S., "Tanibirumab (TTAC-0001): a fully human monoclonal antibody targets vascular endothelial growth factor receptor 2 (VEGFR-2)", Archives of Pharmacal Research, Aug. 2011, pp. 1223-1226, vol. 34, No. 8.
Bray, S., "Notch signalling: a simple pathway becomes complex", "Nature Reviews: Molecular Cell Biology", Sep. 2006, pp. 678-689, vol. 7.
Cao, Y., "Tumor angiogenesis and molecular targets for therapy", "Frontiers in Bioscience", Jan. 1, 2009, pp. 3962-3973, vol. 14.
Carmeliet, P., et al., "Angiogenesis in cancer and other diseases", "Nature", Sep. 14, 2000, pp. 249-257, vol. 407.

(Continued)

Primary Examiner — Ruixiang Li
(74) Attorney, Agent, or Firm — Hultquist, PLLC; Steven J. Hultquist

(57) ABSTRACT

The present invention relates to a novel form of a dual-target antibody targeting VEGFR-2 and DLL4, a gene encoding the same, a recombinant expression vector including the gene, host cells transformed with the recombinant expression vector, a method of producing the dual-target antibody using the host cells, a pharmaceutical composition comprising the dual-target antibody.

4 Claims, 8 Drawing Sheets

(56) References Cited

OTHER PUBLICATIONS

Crawford, Y., et al., "Tumor and stromal pathways mediating refractoriness/resistance to anti-angiogenic therapies", "Trends in Pharmacological Sciences", 2009, pp. 624-630, vol. 30, No. 12.
Duarte, A., et al., "Dosage-sensitive requirement for mouse Dll4 in artery development", "Genes and Development", 2004, pp. 2474-2478, vol. 18.
Dufraine, J., et al., "Notch signaling regulates tumor angiogenesis by diverse mechanisms", "Oncogene", 2008, pp. 5132-5137, vol. 27.
Ellis, L., et al., "VEGF-targeted therapy: mechanisms of anti-tumour activity", "Nature Reviews: Cancer", Jul. 3, 2008, pp. 579-591, vol. 8.
Eter, N., et al., "New Pharmacologic Approaches to Therapy for Age-Related Macular Degeneration", "Biodrugs", 2006, pp. 167-179, vol. 20, No. 3.
Ferrara, N., et al., "Angiogenesis as a therapeutic target", "Nature", Dec. 15, 2005, pp. 967-974, vol. 438.
Ferrara, N., et al., "Bevacizumab (Avastin), a humanized anti-VEGF monoclonal antibody for cancer therapy", "Biochemical and Biophysical Research Communications", Jun. 2, 2005, pp. 328-335, vol. 333.
Gale, N., et al., "Haploinsufficiency of delta-like 4 ligand results in embryonic lethality due to major defects in arterial and vascular development", "PNAS", Nov. 9, 2004, pp. 15949-15954, vol. 101, No. 45.
Ho, M., et al., "2nd PEGS Annual Symposium on Antibodies for Cancer Therapy", "mAbs", Apr. 30-May 1, 2012, pp. 562-570, vol. 4, No. 5, Published in: Boston, MA.
Hoey, T., et al., "DLL4 Blockade Inhibits Tumor Growth and Reduces Tumor-Initiating Cell Frequency", "Cell Stem Cell", Aug. 7, 2009, pp. 168-177, vol. 5.
Holash, J., et al., "VEGF-Trap: A VEGF blocker with potent antitumor effects", "PNAS", Aug. 20, 2002, pp. 11393-11398, vol. 99, No. 17.
Kim, E., et al., "Potent VEGF blockade causes regression of coopted vessels in a model of neuroblastoma", "PNAS", Aug. 20, 2002, pp. 11399-11404, vol. 99, No. 17.
Krebs, L., et al., "Haploinsufficient lethality and formation of arteriovenous malformations in Notch pathway mutants", "Genes and Development", 2004, pp. 2469-2473, vol. 18.
Noguera-Troise, I., et al., "Blockade of Dll4 inhibits tumour growth by promoting non-productive angiogenesis", "Nature", Dec. 28, 2006, pp. 1032-1037, vol. 444, No. 21.
Ridgway, J., et al., "Inhibition of Dll4 signalling inhibits tumour growth by deregulating angiogenesis", "Nature", Dec. 28, 2006, pp. 1083-1087, vol. 444, No. 21.
Risau, W., "Mechanisms of angiogenesis", "Nature", Apr. 17, 1997, pp. 671-674, vol. 386.
Thurston, G., et al., "The Delta paradox: DLL4 blockade leads to more tumour vessels but less tumour growth", "Nature Reviews: Cancer", May 2007, pp. 327-331, vol. 7.
Tischer, E., et al., "The Human Gene for Vascular Endothelial Growth Factor: Multiple Protein Forms are Encoded Through Alternative Exon Splicing", "The Journal of Biological Chemistry", Jun. 25, 1991, pp. 11947-11954, vol. 266, No. 18.
Wang, Z., et al., "Targeting Notch signaling pathway to overcome drug resistance for cancer therapy", "Biochimica et Biophysica Acta", Jun. 22, 2010, pp. 258-267, vol. 1806.
Youssoufian, H., et al., "Review: Monoclonal Antibodies to the Vascular Endothelial Growth Factor Receptor-2 in Cancer Therapy", "Clin Cancer Res", Sep. 15, 2007, p. 5544s-5548s (18 Supplement), vol. 13.
NOTE: For the non-patent literature citations that no month of publication is indicated, the year of publication is more than 1 year prior to the effective filing date of the present application.
Laura A. Sullivan et al., "The VEGF family in cancer and antibody-based strategies for their inhibition", Mar. 2010, pp. 165-175, vol. 2, No. 2, Landes Bioscience, www.landesbioscience.com.
Sheldon, H., et al., "New mechanism for Notch signaling to endothelium at a distance by Delta-like 4 incorporation into exosomes", "Blood", Sep. 30, 2010, pp. 2385-2394, vol. 116, No. 13.

DVDEC SLGAN PCEHA GKCIN
TLGSF ECQCL QGYTG PRCEI
DVNEC VSNPC QNDAT CLDQI
GEFQC ICMPG YEGVH CE

Binding Affinity of PMC-201 to human Ag-X (Biacore)

| | Ka(1/Ms) | Kd(1/s) | KD (M) |
|---|---|---|---|
| PMC-201 | 2.74 X10$^4$ | 3.88 X10$^{-4}$ | 1.42 X10$^{-8}$ |
| Human Notch1-Fc | 6.09 X10$^4$ | 1.22 X10$^{-3}$ | 1.99 X10$^{-8}$ |

SEQUENCE LISTING

```
<160> NUMBER OF SEQ ID NOS: 12

<210> SEQ ID NO 1
<211> LENGTH: 122
<212> TYPE: PRT
<213> ORGANISM: Artificial Sequence
<220> FEATURE:
<223> OTHER INFORMATION: anti-VEGFR-2 variable heavy chain

<400> SEQUENCE: 1

Ala Gln Pro Ala Met Ala Gln Met Gln Leu Val Gln Ser Gly Ala Glu
1               5                   10                  15

Val Lys Lys Pro Gly Ala Ser Val Lys Leu Ser Cys Lys Ala Ser Gly
            20                  25                  30

Tyr Thr Phe Ser Ser Tyr Trp Met His Trp Val Arg Gln Ala Pro Gly
        35                  40                  45

Gln Arg Leu Glu Trp Met Gly Glu Ile Asn Pro Gly Asn Gly His Thr
    50                  55                  60

Asn Tyr Asn Glu Lys Phe Lys Ser Arg Val Thr Ile Thr Val Asp Lys
65                  70                  75                  80

Ser Ala Ser Thr Ala Tyr Met Glu Leu Ser Ser Leu Arg Ser Glu Asp
                85                  90                  95

Thr Ala Val Tyr Tyr Cys Ala Lys Ile Trp Gly Pro Ser Leu Thr Ser
            100                 105                 110

Pro Phe Asp Tyr Trp Gly Gln Gly Thr Leu
        115                 120

<210> SEQ ID NO 2
<211> LENGTH: 116
<212> TYPE: PRT
<213> ORGANISM: Artificial Sequence
```

```
<220> FEATURE:
<223> OTHER INFORMATION: anti-VEGFR-2 variable heavy chain

<400> SEQUENCE: 2

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Arg Leu Glu Trp Met
        35                  40                  45

Gly Glu Ile Asn Pro Gly Asn Gly His Thr Asn Tyr Asn Glu Lys Phe
    50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Ile Trp Gly Pro Ser Leu Thr Ser Pro Phe Asp Tyr Trp Gly
            100                 105                 110

Gln Gly Thr Leu
        115

<210> SEQ ID NO 3
<211> LENGTH: 116
<212> TYPE: PRT
<213> ORGANISM: Artificial Sequence
<220> FEATURE:
<223> OTHER INFORMATION: anti-VEGFR-2 variable heavy chain

<400> SEQUENCE: 3

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Arg Leu Glu Trp Met
        35                  40                  45

Gly Glu Ile Asn Pro Gly Asn Gly His Thr Asn Tyr Asn Glu Lys Phe
    50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Ile Trp Gly Pro Ser Leu Thr Ser Pro Phe Asp Tyr Trp Gly
            100                 105                 110

Gln Gly Thr Leu
        115

<210> SEQ ID NO 4
<211> LENGTH: 113
<212> TYPE: PRT
<213> ORGANISM: Artificial Sequence
<220> FEATURE:
<223> OTHER INFORMATION: anti-VEGFR-2 variable light chain

<400> SEQUENCE: 4

Ser Gly Val Gly Ser Asn Phe Met Leu Thr Gln Pro Pro Ser Val Ser
1               5                   10                  15

Val Ser Pro Gly Lys Thr Ala Arg Ile Thr Cys Arg Gly Asp Asn Leu
            20                  25                  30
```

```
Gly Asp Val Asn Val His Trp Tyr Gln Gln Arg Pro Gly Gln Ala Pro
        35                  40                  45

Val Leu Val Met Tyr Tyr Asp Ala Asp Arg Pro Ser Gly Ile Pro Glu
 50                  55                  60

Arg Phe Ser Gly Ser Asn Ser Gly Asn Thr Ala Thr Leu Thr Ile Ser
 65                  70                  75                  80

Gly Val Glu Ala Gly Asp Glu Ala Asp Tyr Tyr Cys Gln Val Trp Asp
                 85                  90                  95

Arg Thr Ser Glu Tyr Val Phe Gly Thr Gly Thr Lys Val Thr Val Leu
            100                 105                 110

Gly

<210> SEQ ID NO 5
<211> LENGTH: 108
<212> TYPE: PRT
<213> ORGANISM: Artificial Sequence
<220> FEATURE:
<223> OTHER INFORMATION: anti-VEGFR-2 variable light chain

<400> SEQUENCE: 5

Asn Phe Met Leu Thr Gln Pro Pro Ser Val Ser Val Ser Pro Gly Lys
 1               5                  10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
 50                  55                  60

Asn Ser Gly Asn Thr Ala Thr Leu Thr Ile Ser Gly Val Glu Ala Gly
 65                  70                  75                  80

Asp Glu Ala Asp Tyr Tyr Cys Gln Val Trp Asp Arg Thr Ser Glu Tyr
                 85                  90                  95

Val Phe Gly Thr Gly Thr Lys Val Thr Val Leu Gly
            100                 105

<210> SEQ ID NO 6
<211> LENGTH: 109
<212> TYPE: PRT
<213> ORGANISM: Artificial Sequence
<220> FEATURE:
<223> OTHER INFORMATION: anti-VEGFR-2 variable light chain

<400> SEQUENCE: 6

Asn Phe Met Leu Thr Gln Pro Pro Ser Val Ser Val Ser Pro Gly Lys
 1               5                  10                  15

Thr Ala Arg Ile Thr Cys Arg Gly Asp Asn Leu Gly Asp Val Asn Val
            20                  25                  30

His Trp Tyr Gln Gln Arg Pro Gly Gln Ala Pro Val Leu Val Met Tyr
        35                  40                  45

Tyr Asp Ala Asp Arg Pro Ser Gly Ile Pro Glu Arg Phe Ser Gly Ser
 50                  55                  60

Asn Ser Gly Asn Thr Ala Thr Leu Thr Ile Ser Gly Val Glu Ala Gly
 65                  70                  75                  80

Asp Glu Ala Asp Tyr Tyr Cys Gln Val Trp Asp Arg Thr Ser Glu Tyr
                 85                  90                  95

Val Phe Gly Thr Gly Thr Lys Val Glu Ile Lys Arg Thr
            100                 105
```

<210> SEQ ID NO 7
<211> LENGTH: 77
<212> TYPE: PRT
<213> ORGANISM: Artificial Sequence
<220> FEATURE:
<223> OTHER INFORMATION: Notch1 minimal decoy

<400> SEQUENCE: 7

Asp Val Asp Glu Cys Ser Leu Gly Ala Asn Pro Cys Glu His Ala Gly
1               5                   10                  15

Lys Cys Ile Asn Thr Leu Gly Ser Phe Glu Cys Gln Cys Leu Gln Gly
            20                  25                  30

Tyr Thr Gly Pro Arg Cys Glu Ile Asp Val Asn Glu Cys Val Ser Asn
        35                  40                  45

Pro Cys Gln Asn Asp Ala Thr Cys Leu Asp Gln Ile Gly Glu Phe Gln
    50                  55                  60

Cys Ile Cys Met Pro Gly Tyr Glu Gly Val His Cys Glu
65                  70                  75

<210> SEQ ID NO 8
<211> LENGTH: 13
<212> TYPE: PRT
<213> ORGANISM: Artificial Sequence
<220> FEATURE:
<223> OTHER INFORMATION: amino acid linker

<400> SEQUENCE: 8

Ser Gly Gly Gly Gly Ser Gly Gly Gly Gly Ser Gly Ser
1               5                   10

<210> SEQ ID NO 9
<211> LENGTH: 198
<212> TYPE: PRT
<213> ORGANISM: Artificial Sequence
<220> FEATURE:
<223> OTHER INFORMATION: bispecific antibody (light chain-Notch1 minimal
      decoy)

<400> SEQUENCE: 9

Asp Val Asp Glu Cys Ser Leu Gly Ala Asn Pro Cys Glu His Ala Gly
1               5                   10                  15

Lys Cys Ile Asn Thr Leu Gly Ser Phe Glu Cys Gln Cys Leu Gln Gly
            20                  25                  30

Tyr Thr Gly Pro Arg Cys Glu Ile Asp Val Asn Glu Cys Val Ser Asn
        35                  40                  45

Pro Cys Gln Asn Asp Ala Thr Cys Leu Asp Gln Ile Gly Glu Phe Gln
    50                  55                  60

Cys Ile Cys Met Pro Gly Tyr Glu Gly Val His Cys Glu Ser Gly Gly
65                  70                  75                  80

Gly Gly Ser Gly Gly Gly Gly Ser Gly Ser Asn Phe Met Leu Thr Gln
            85                  90                  95

Pro Pro Ser Val Ser Val Ser Pro Gly Lys Thr Ala Arg Ile Thr Cys
        100                 105                 110

Arg Gly Asp Asn Leu Gly Asp Val Asn Val His Trp Tyr Gln Gln Arg
    115                 120                 125

Pro Gly Gln Ala Pro Val Leu Val Met Tyr Tyr Asp Ala Asp Arg Pro
    130                 135                 140

Ser Gly Ile Pro Glu Arg Phe Ser Gly Ser Asn Ser Gly Asn Thr Ala
145                 150                 155                 160

```
Thr Leu Thr Ile Ser Gly Val Glu Ala Gly Asp Glu Ala Asp Tyr Tyr
                165                 170                 175

Cys Gln Val Trp Asp Arg Thr Ser Glu Tyr Val Phe Gly Thr Gly Thr
            180                 185                 190

Lys Val Thr Val Leu Gly
        195

<210> SEQ ID NO 10
<211> LENGTH: 199
<212> TYPE: PRT
<213> ORGANISM: Artificial Sequence
<220> FEATURE:
<223> OTHER INFORMATION: bispecific antibody (light chain-Notch1 minimal
      decoy)

<400> SEQUENCE: 10

Asp Val Asp Glu Cys Ser Leu Gly Ala Asn Pro Cys Glu His Ala Gly
1               5                   10                  15

Lys Cys Ile Asn Thr Leu Gly Ser Phe Glu Cys Gln Cys Leu Gln Gly
            20                  25                  30

Tyr Thr Gly Pro Arg Cys Glu Ile Asp Val Asn Glu Cys Val Ser Asn
        35                  40                  45

Pro Cys Gln Asn Asp Ala Thr Cys Leu Asp Gln Ile Gly Glu Phe Gln
    50                  55                  60

Cys Ile Cys Met Pro Gly Tyr Glu Gly Val His Cys Glu Ser Gly Gly
65                  70                  75                  80

Gly Gly Ser Gly Gly Gly Ser Gly Ser Asn Phe Met Leu Thr Gln
                85                  90                  95

Pro Pro Ser Val Ser Val Ser Pro Gly Lys Thr Ala Arg Ile Thr Cys
            100                 105                 110

Arg Gly Asp Asn Leu Gly Asp Val Asn Val His Trp Tyr Gln Gln Arg
        115                 120                 125

Pro Gly Gln Ala Pro Val Leu Val Met Tyr Tyr Asp Ala Asp Arg Pro
    130                 135                 140

Ser Gly Ile Pro Glu Arg Phe Ser Gly Ser Asn Ser Gly Asn Thr Ala
145                 150                 155                 160

Thr Leu Thr Ile Ser Gly Val Glu Ala Gly Asp Glu Ala Asp Tyr Tyr
                165                 170                 175

Cys Gln Val Trp Asp Arg Thr Ser Glu Tyr Val Phe Gly Thr Gly Thr
            180                 185                 190

Lys Val Glu Ile Lys Arg Thr
        195

<210> SEQ ID NO 11
<211> LENGTH: 2058
<212> TYPE: DNA
<213> ORGANISM: Artificial Sequence
<220> FEATURE:
<223> OTHER INFORMATION: human DLL4 DNA sequence

<400> SEQUENCE: 11
atggccgctg ccagcagatc tgcctctggc tgggctctgc tgctgctggt ggctctgtgg        60
cagcagagag ccgccggaag cggcgtgttc cagctgcagc tccaggagtt catcaacgag       120
cggggcgtgc tggccagcgg cagaccttgt gaacccggct gccggacctt cttcagagtg       180
tgcctgaagc acttccaggc cgtggtgtcc cccggaccct gcaccttgg caccgtgtcc       240 acaccegtge tgggcaccaa cagcttcgcc gtgcgggacg atagcagcgg cggaggcaga       300
```

| | | |
|---|---|---|
| aacccccctgc agctgcccctt caacttcacc tggcccggca ccttcagcct gatcatcgag | 360 | |
| gcctggcacg ccccctggcga cgacctgagg cctgaagccc tgcctcccga cgccctgatc | 420 | |
| agcaagatcg ccatccaggg cagcctggcc gtgggccaga actggctgct ggacgagcag | 480 | |
| accagcaccc tgacccggct gcggtacagc tacagagtga tctgcagcga caactactac | 540 | |
| ggcgacaact gcagccggct gtgcaagaag cggaacgacc acttcggcca ctacgtgtgc | 600 | |
| cagcccgacg caacctgag ctgcctgcct ggatggaccg gcgagtactg ccagcagccc | 660 | |
| atctgcctga gcggctgcca cgagcagaac ggctactgca gcaagcccgc cgagtgcctg | 720 | |
| tgcagacctg gctggcaggg cagactgtgc aacgagtgca tcccccacaa cggctgccgg | 780 | |
| cacggcacct gtagcacccc ctggcagtgc acctgtgacg agggctgggg cggactgttc | 840 | |
| tgtgatcagg acctgaacta ctgcacccac acagcccct gcaagaacgg cgccacatgc | 900 | |
| agcaacagcg gccagcggag ctacacctgt acctgcagac ccggctacac cggcgtggac | 960 | |
| tgcgagctgg aactgagcga gtgcgacagc aaccccctgcc ggaatggcgg cagctgcaag | 1020 | |
| gaccaggaag atggctacca ctgcctgtgc ccccctggct actacggcct gcactgcgag | 1080 | |
| cacagcaccc tgtcctgcgc cgactcccc tgctttaacg gcggctcctg cagagagcgg | 1140 | |
| aaccagggcg ccaactacgc ctgcgagtgc cccccaatt tcaccggcag caactgcgag | 1200 | |
| aagaaagtgg accggtgcac ctccaacccc tgcgccaatg gcggacagtg cctgaacaga | 1260 | |
| ggccccagcc ggatgtgcag atgcaggcct ggcttcaccg gcacctattg cgagctgcac | 1320 | |
| gtgtccgact gcgcccggaa tccttgtgcc cacggcggca cctgtcacga cctggaaaac | 1380 | |
| ggcctgatgt gcacctgtcc tgccggcttc agcgggcgga gatgcgaagt gcggaccagc | 1440 | |
| atcgatgcct gcgcctccag cccctgcttc aaccgggcca cctgttacac cgacctgagc | 1500 | |
| accgacacct tcgtgtgcaa ctgccccta cggcttcgtgg gcagcagatg cgagttcccc | 1560 | |
| gtgggcctgc cccccagctt tccttgggtg gccgtgtctc tgggcgtggg cctggctgtg | 1620 | |
| ctgctggtcc tgctgggaat ggtggccgtg gctgtgcggc agctgagact gagaaggccc | 1680 | |
| gacgacggca gccgcgaggc catgaacaac ctgagcgact tccagaagga caacctgatc | 1740 | |
| cctgccgccc agctgaagaa caccaaccag aaaaaagagc tggaagtcga ctgcggcctg | 1800 | |
| gacaagagca actgcggcaa gcagcagaac cacacccctgg actacaacct ggcccctggc | 1860 | |
| cctctgggca gccaccat gcctggcaag ttcccccaca gcgacaagag cctgggcgag | 1920 | |
| aaggcccccc tgagactgca cagcgagaag cccgagtgcc ggatcagcgc catctgcagc | 1980 | |
| cccagagaca gcatgtacca gagcgtgtgc ctgatctccg aggaacggaa cgagtgcgtg | 2040 | |
| atcgccaccg aagtgtga | 2058 | |

<210> SEQ ID NO 12
<211> LENGTH: 685
<212> TYPE: PRT
<213> ORGANISM: Artificial Sequence
<220> FEATURE:
<223> OTHER INFORMATION: human DLL4 amino acid sequence

<400> SEQUENCE: 12

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
        35                  40                  45

```
Pro Cys Glu Pro Gly Cys Arg Thr Phe Phe Arg Val Cys Leu Lys His
 50              55                  60
Phe Gln Ala Val Val Ser Pro Gly Pro Cys Thr Phe Gly Thr Val Ser
 65              70                  75                      80
Thr Pro Val Leu Gly Thr Asn Ser Phe Ala Val Arg Asp Asp Ser Ser
                 85                  90                  95
Gly Gly Gly Arg Asn Pro Leu Gln Leu Pro Phe Asn Phe Thr Trp Pro
                100             105                 110
Gly Thr Phe Ser Leu Ile Ile Glu Ala Trp His Ala Pro Gly Asp Asp
                115             120                 125
Leu Arg Pro Glu Ala Leu Pro Pro Asp Ala Leu Ile Ser Lys Ile Ala
    130             135                 140
Ile Gln Gly Ser Leu Ala Val Gly Gln Asn Trp Leu Leu Asp Glu Gln
145             150                 155                     160
Thr Ser Thr Leu Thr Arg Leu Arg Tyr Ser Tyr Arg Val Ile Cys Ser
                165                 170                 175
Asp Asn Tyr Tyr Gly Asp Asn Cys Ser Arg Leu Cys Lys Lys Arg Asn
                180                 185                 190
Asp His Phe Gly His Tyr Val Cys Gln Pro Asp Gly Asn Leu Ser Cys
                195                 200                 205
Leu Pro Gly Trp Thr Gly Glu Tyr Cys Gln Gln Pro Ile Cys Leu Ser
    210             215                 220
Gly Cys His Glu Gln Asn Gly Tyr Cys Ser Lys Pro Ala Glu Cys Leu
225             230                 235                     240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
                260                 265                 270
Asp Glu Gly Trp Gly Gly Leu Phe Cys Asp Gln Asp Leu Asn Tyr Cys
                275                 280                 285
Thr His His Ser Pro Cys Lys Asn Gly Ala Thr Cys Ser Asn Ser Gly
    290                 295                 300
Gln Arg Ser Tyr Thr Cys Thr Cys Arg Pro Gly Tyr Thr Gly Val Asp
305                 310                 315                 320
Cys Glu Leu Glu Leu Ser Glu Cys Asp Ser Asn Pro Cys Arg Asn Gly
                325                 330                 335
Gly Ser Cys Lys Asp Gln Glu Asp Gly Tyr His Cys Leu Cys Pro Pro
                340                 345                 350
Gly Tyr Tyr Gly Leu His Cys Glu His Ser Thr Leu Ser Cys Ala Asp
                355                 360                 365
Ser Pro Cys Phe Asn Gly Gly Ser Cys Arg Glu Arg Asn Gln Gly Ala
    370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
                420                 425                 430
Thr Gly Thr Tyr Cys Glu Leu His Val Ser Asp Cys Ala Arg Asn Pro
                435                 440                 445
Cys Ala His Gly Gly Thr Cys His Asp Leu Glu Asn Gly Leu Met Cys
    450                 455                 460
Thr Cys Pro Ala Gly Phe Ser Gly Arg Arg Cys Glu Val Arg Thr Ser
```

-continued

```
465                 470                 475                 480
Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
                500                 505                 510

Val Gly Ser Arg Cys Glu Phe Pro Val Gly Leu Pro Pro Ser Phe Pro
                515                 520                 525

Trp Val Ala Val Ser Leu Gly Val Gly Leu Ala Val Leu Leu Val Leu
                530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
                580                 585                 590

Glu Leu Glu Val Asp Cys Gly Leu Asp Lys Ser Asn Cys Gly Lys Gln
                595                 600                 605

Gln Asn His Thr Leu Asp Tyr Asn Leu Ala Pro Gly Pro Leu Gly Arg
                610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
                660                 665                 670

Ser Glu Glu Arg Asn Glu Cys Val Ile Ala Thr Glu Val
                675                 680                 685
```

DUAL-TARGET ANTIBODY TARGETING VEGFR-2 AND DLL4, AND PHARMACEUTICAL COMPOSITION INCLUDING SAME

CROSS-REFERENCE TO RELATED APPLICATIONS

This application is a U.S. national phase under the provisions of 35 U.S.C. § 371 of International Patent Application No. PCT/KR2013/010589 filed Nov. 20, 2013, which in turn claims priority of Korean Patent Application No. 10-2012-0132431 filed Nov. 21, 2012. The disclosures of such international patent application and Korean priority patent application are hereby incorporated herein by reference in their respective entireties, for all purposes.

TECHNICAL FIELD

The present invention relates to a novel form of a dual-target antibody in which an antagonist of DLL4 is bound to a terminal of an antibody targeting VEGFR-2 to additionally target human DLL4, DNA encoding the antibody, a recombinant expression vector including the same, host cells transformed with the recombinant expression vector, a method of producing the dual-target antibody using the host cells, a pharmaceutical composition including the dual-target antibody, and a method of measuring a DLL4 antagonist efficacy of the dual-target antibody.

BACKGROUND ART

Angiogenesis is a mechanism in which new blood vessels are generated from existing blood vessels by growth, division, migration, and the like, of an endothelial cell, plays an important roll in normal growth processes including wound healing or female menstrual cycle (Risau, *Nature*, 386:671, 1997), and moreover, abnormally excessive angiogenesis is known to play a crucial role in diseases such as tumor growth and metastasis, age-related macular degeneration (ARMD), diabetic retinopathy, psoriasis, rheumatoid arthritis and chronic inflammation (Carmeliet and Jain, *Nature*, 407:249, 2000).

Hypothesis that tumor growth and metastasis are angiogenesis dependent, and therefore, a therapy focusing on anti-angiogenesis could be a new therapeutic agent for solid tumors was raised by Dr. J. Folkman in 1971. Afterthat, research into a technology relating to inhibition of excessive angiogenesis mechanisms has attracted attention of many researchers (Ferrara and Kerbel, *Nature*, 438:967, 2005). A progressing aspect of the angiogenesis is determined by comprehensive balance of angiogenesis inducers and angiogenesis inhibitors, and is progressed by complex and multi-step sequential processes. In detail, various angiogenesis inducers including vascular endothelial growth factor (VEGF) secreted by tumor or injured tissues are bound to corresponding receptors of existing peripheral vascular endothelial cells to activate vascular endothelial cells, which increase permeability of vascular endothelial cells, and to secret protease such as matrix metalloproteinase (MMP), which decomposes basement membrane and extracellular matrix surrounding vascular endothelial cells, such that the vascular endothelial cells escape from existing capillaries and migrate/proliferate toward the tissue secreting angiogenesis inducer. The migrated and proliferated vascular endothelial cells form an intravascular tube structure, and finally, pericyte which is a structural support of the vascular endothelial cell is introduced to achieve stable and mature blood vessel formation.

As described above, it was found that signaling of VEGF and a VEGF receptor (VEGFR) bound to the VEGF is suppressed to ultimately inhibit angiogenesis, thereby obtaining therapeutic effects on various diseases age-related macular degeneration, diabetic retinopathy, psoriasis, rheumatoid arthritis and chronic inflammation, including growth and metastasis of tumor, and thus, development of various drugs capable of inhibiting VEGF activity has been ongoing.

Specifically, VEGF forms protein separation and purification and cDNA cloning by Dr. N. Ferrara group from Genentech in 1989 (Leung et al., *Science*, 246:1306, 1989). It is known so far that VEGF which is also referred to as VEGF-A has four isotypes (VEGF121, VEGF165, VEGF189, and VEGF206), and it is reported that among the four isotypes, VEGF165 is the most abundant in all human tissues except for placenta (Tisher et al., *J. Biol. Chem.*, 266:11947, 1991). It is known that VEGF is bound to receptors VEGFR-1 and VEGFR-2/KDR with significantly high affinity; however, signal of VEGF is mainly transferred through VEGFR-2 to induce mechanisms related to angiogenesis such as proliferation, migration, and the like, of vascular endothelial cells. Due to the above-described reasons, VEGF and VEGFR-2 become main targets for inhibiting angiogenesis mechanism induced by VEGF, and a number of theses deal with VEGF and VEGFR-2 (Ellis and Hicklin, *Nature Rev. Cancer*, 8:579, 2008; Youssoufian et al., *Clin. Cancer Res.*, 13:5544s, 2007).

For example, Avastin (bevacizumab, Genentech) is a humanized antibody targeting VEGF-A (Ferrara et al., *Biochem. Biophy. Res. Comm.*, 333:328, 2005), which has received US FDA approval on treatment for metastatic colorectal cancer in 2004, non-small cell lung cancer in 2006, and Her-2 negative metastatic breast cancer in 2008, respectively, and is approved to treat Glioblastoma mutiforme (GBM), and renal cancer. Currently, clinical trials on a variety of solid tumors are ongoing in order to expand indications. In addition, Lucentis which was developed in the same company, is an antibody prepared by cutting Fab fragments only from Avastin for good permeability of Lucentis when Lucentis is injected into retina in order to inhibit excessive angiogenesis around macula which is a main aspect of senile macular degeneration (Eter et al, *Biodrugs*, 20:167, 2006), and as a therapeutic agent for wet age-related macular degeneration (wet-ARMD), which has received US FDA approval in 2006.

As another antibody for treatment targeting VEGF, there is VEGF-trap manufactured by Regeneron (Holash et al., *PNAS*, 99:11393, 2002). VEGF-trap is a soluble decoy receptor in a form in which second immunoglobulin domain of VEGFR-1 and third immunoglobulin domain of VEGFR-2 are fused to human Fc, which has not received U.S. FDA approval yet, but has been ongoing in phase III stage for metastatic breast cancer, metastatic lung cancer, metastatic colorectal cancer, hormone refractory prostate cancer, and the like.

Meanwhile, examples of anti-angiogenesis antibodies targeting VEGFR-2 which is a receptor of VEGF include IMC-1121B (EP 1916001A2) manufactured by Imclone company, CDP-791 (PCT/GB02/04619) manufactured by UCB company, Tanibirumab (TTAC-0001) (WO2008/153237) developed by the present inventors and has been in a clinical trial, and the like.

IMC-1121B is a monoclonal antibody selected from a fully human Fab library, which has been ongoing in Phase III stage for metastatic breast cancer, and was entered in Phase III stage for stomach cancer in 2010. CDP-791 manufactured by UCB is a humanized antibody, which has been ongoing in phase II stage for non-small cell lung cancer in PEGylated Di-Fab form. Since this antibody does not have Fc, antibody-dependent cell-mediated cytotoxicity or complement-dependent cytotoxicity may not be expected.

Lastly, Tanibirumab (TTAC-0001) developed by the present inventors is a monoclonal antibody selected from a fully human ScFv library, and is the only antibody having reactivity with flk-1 of mouse and rat origin (VEGFR-2 homologue) while simultaneously targeting VEGFR-2, which is one of important distinguishable features from IMC-1121B manufactured by Imclone (WO02008/153237). In particular, cross-species cross reactivity exhibited by Tanibirumab is possible to make a research into animal disease model to carry on future development of anti-cancer agent for specific cancer by stages, which makes related researches easier.

As described above, researches targeting VEGF and VEGFR-2 have been dramatically developed for last five years, and a number of therapeutic agents are developed by market and clinical studies.

Meanwhile, cells differentiated into Tip cell by VEGF/VEGFR-2 signaling strongly express DLL4 and are bound to Notch1 receptor present in surrounding cells, and cells in which Notch1 signaling pathway is activated are differentiated into stalk cells to form normal blood vessel tube structure, which proves that DLL4/Notch1 signaling pathway is one of the most important mechanisms for VEGF/VEGFR-2 path and angiogenesis (Dufraine et al., *Oncogene*, 27:5132-5137, 2008).

It is known so far that DLL4 is one of ligands to a Notch receptor, and there are four kinds of Notch receptors (Notch 1 to 4) and five kinds of Notch ligands (Jagged-1, Jagged-2, DLL1, DLL3, and DLL4) in mammals. Notch signaling pathway is initiated by binding a Notch ligand of one cell to a Notch receptor of other cell, and is necessarily activated only by direct interaction between different cells (Bray S J, *Nat Rev Mol Cell Biol.*, 7(9):678, 2006).

When the Notch ligand is bound to the Notch receptor, an ADAM metalloprotease is firstly activated to cleave a cellular membrane outer proximal site of the Notch receptor, and then a gamma-secretase complex is activated to cleave a cellular membrane inner proximal site of the Notch receptor, such that Notch Intracellular Domain (NICD) is isolated and migrates into the nucleus. NICD is bound to an RBPJ/CSL transcription factor to induce expression of Notch target genes such as basic helix-loop-helix proteins including Hes and Hey. The Notch signaling pathway determines proliferation/differentiation/apoptosis in accordance with the situation of corresponding cells, and plays an important role in maintenance of normal stem cells and cancer stem cells.

Basically, all Notch receptors are capable of being bound to all Notch ligands; however, combinations of various bindings are selectively controlled in microenvironments of the corresponding cells. For example, DLL4 is strongly expressed on angiogenesis endothelial cells during a fetal development process, and is bound to Notch1 and Notch4 which are expressed in peripheral endothelial cells; however, DLL4-Notch1 binding is the most important in an exclusive way (Yan M, Vasc Cell, 2011), and angiogenesis progresses through the DLL4-Notch1 binding. The above-description is well found by gene deficiency test, and the like (Duarte et al., *Genes Dev,* 2004; Gale et al., *PNAS,* 2004; Krebs et al., *Genes Dev,* 2004).

Therefore, when the DLL4-Notch1 binding is suppressed, angiogenesis may be inhibited, and therefore, various diseases such as tumor, and the like, are capable of being treated. It has been already proven that when VEGF is inhibited by using Avastin (bevacizumab), and the like, in cancer treatment, angiogenesis is inhibited to decrease perfusion of the tumor, and a tumor size is decreased. Meanwhile, when binding with Notch1 expressed in peripheral cells while targeting DLL4 is inhibited, blood vessels are abnormally and largely generated (hypersprouting), but do not achieve complete function, which decreases perfusion of non-functional tumor, and as a result, the tumor size is reduced (Thurston et al., *Nat Rev Cancer,* 7(5):327, 2007).

Interestingly, when an antibody inhibiting VEGF and DLL4 is administered in xenograft animal experiments using several cancer cell lines performed in Genentech's research team, growth of the cancer is much strongly suppressed, as compared to a case in which an antibody inhibiting VEGF and an antibody inhibiting DLL4 are separately administered, respectively (Ridgway et al., *Nature,* 444(7122):1083, 2006). It suggests that signaling by DLL4/Notch1 path is not simply activated by VEGF/VEGFR-2 path, and various angiogenesis-related diseases such as tumor, and the like, are capable of being effectively treated by simultaneously inhibiting signalings by two paths.

In addition, it was found that DLL4 inhibition has an effect on both of a tumor being sensitive to VEGF/VEGFR-2 path inhibitor and a tumor being resistant to VEGF/VEGFR-2 path inhibitor (Ridgway et al., *Nature.,* 444 (7122):1083, 2006; Noguera-Troise et al., *Nature.,* 444 (7122):1032. 2006), which provides a significantly important clue to overcome resistance which currently and frequently occurs when drugs such as Avastin blocking VEGF are administered (including two cases of an intrinsic resistance in which Avastin is not effective from the beginning and acquired resistance in which an efficacy of Avastin is gradually falling over time).

Further, it was found from Oncomed's research team that DLL4 inhibition directly reduces frequency of cancer stem cells in tumor and inhibits tumor growth (Hoey et al., *Cell Stem Cell.,* 2009), which suggests that DLL4 inhibition is possible to essentially block recurrence of cancer. Finally, resistance to anti-cancer chemotherapy and antibody therapeutic agents such as Herceptin, and the like, that are currently used for cancer treatment has a lot of relevance to the Notch signaling pathway and inhibition of DLL4/Notch1 path is also possible to overcome resistance of the anti-cancer chemotherapy and the antibody therapeutic agents such as Herceptin, and the like (Wang et al., *Biochim Biophys Acta.,* 1806(2):258, 2010).

As described above, various angiogenesis-related diseases such as tumor, and the like, are capable of being effectively treated by simultaneously inhibiting signalings by two paths of VEGF/VEGFR-2 and DLL4/Notch 1. However, the development of drugs that are effective for this has not been made yet, and therefore, relevant development is urgently required.

SUMMARY OF INVENTION

The present inventors conducted a research into development of a therapeutic agent capable of treating various angiogenesis-related diseases such as tumor, and the like, by more effectively and simultaneously suppressing signaling of two paths, VEGF/VEGFR-2 and DLL4/Notch1 to solve the above-described problems, and as a result, found that a dual-target antibody simultaneously targeting VEGFR-2 and DLL4 effectively exhibits an effect of treating various angiogenesis-related diseases, and completed the present invention.

An object of the present invention is to provide a dual-target antibody simultaneously targeting VEGFR and DLL4 by binding an antibody to VEGFR-2 and an antagonist to DLL4.

Another object of the present invention is to provide DNA encoding the dual-target antibody, and a recombinant expression vector including the same.

Another object of the present invention is to provide host cells transformed with the recombinant expression vector, and a method of producing the dual-target antibody according to the present invention, by using the host cells.

Another object of the present invention is to provide a pharmaceutical composition for treating angiogenesis related diseases comprising the dual-target antibody.

BEST MODE

Figures 1, 2:
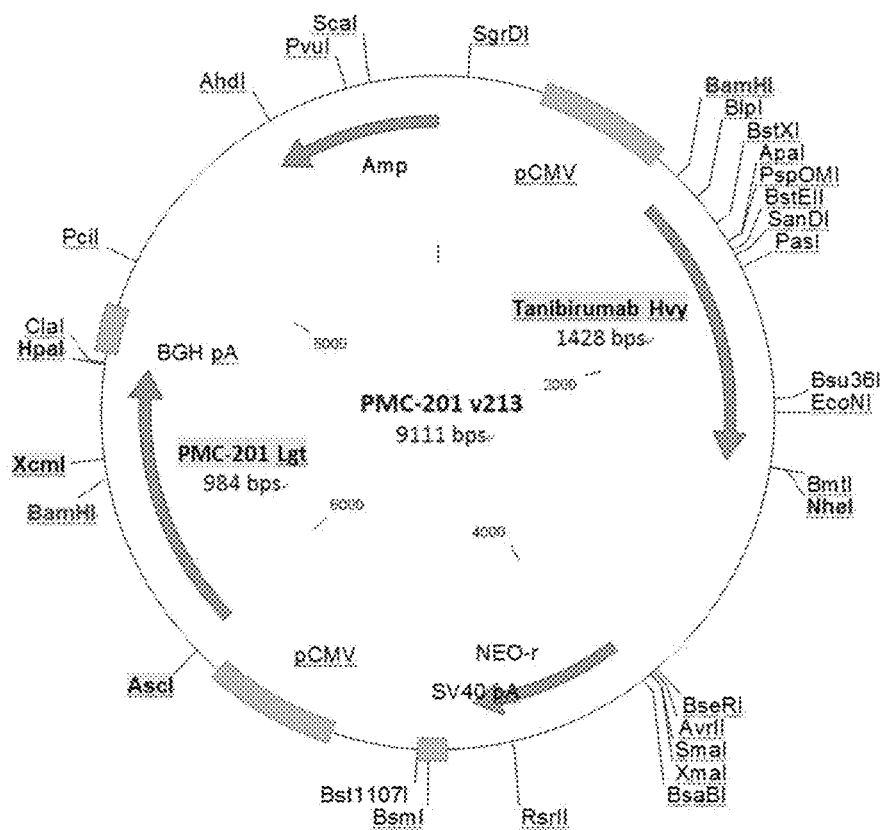
FIG. 1 represents amino acid sequence (SEQ ID NO: 7) of EGF-like domains 11 and 12 of Notch1 bound to DLL4.
FIG. 2 is a diagram of a vector PMC-201 v213 according to the present invention.

As far as it is not defined in other ways, all technical and scientific terms used in the present specification have the same meaning as being generally appreciated by those skilled in the art to which the present invention pertains. In general, a nomenclature used in the present specification and experimental methods that are described below are well known in the present technical field and generally used.

In an embodiment for achieving objects of the present invention, the present invention provides a dual-target antibody in which an antagonist of DLL4 is bound to a terminal of an antibody specifically bound to VEGFR-2.

It was confirmed that the dual-target antibody according to the present invention has an effects of inhibiting diseases caused by angiogenesis, by more effectively inhibiting angiogenesis, and has a binding affinity to each of targets VEGFR-2 and DLL4. In addition, it was confirmed from HUVEC proliferation inhibitory experiment that the dual-target antibody according to the present invention has excellent HUVEC proliferation inhibitory ability as compared to an antibody single-targeting VEGFR-2 only, for example, Tanibirumab.

In the invention, a term "dual-target antibody" means an antibody having a binding affinity or antagonism to one or more targets, and means an antibody in which two antibodies having a binding affinity or antagonism to different targets are bound to each other or an antibody having a binding affinity to one target is bound to a material having antagonism to the other target.

In addition, in the present invention, a term "antibody" includes both of polyclonal antibody and monoclonal antibody, wherein a fragment of an antibody molecule as well as a complete form including two light chains having the entire length and two heavy chains having the entire length may be used. The fragment of the antibody molecule means a fragment necessarily possessing an antigen binding function and includes a single-chain, Fv(scFv), Fab, F(ab'), F(ab')$_2$, a single domain, and the like.

Preferably, the dual-target antibody according to the invention has a form in which an antibody which is specific for an angiogenesis factor or a receptor for such angiogenesis factor is bound to an angiogenesis antagonist, that is, an antagonist to an angiogenesis factor or a receptor for such angiogenesis factor.

In the dual-target antibody according to the invention, the antibody specifically bound to VEGFR-2 is usable without limitation as long as it is an antibody which is bound to the VEGFR-2 to inhibit VEGF/VEGFR-2 signaling, preferably, Tanibirumab or Bevacizumab, or variants thereof, but the present invention is not limited thereto.

In addition, the antagonist of DLL4 is usable without limitation as long as it is a substance having property of inhibiting DLL4/Notch1 signaling, particularly, a soluble receptor of which a cellular domain of Notch1 is deleted is preferred, but the present invention is not limited thereto. More preferably, as the antagonist of DLL4, 11st and 12nd EGF-like domains of a Notch1 receptor to DLL4 (hereinafter, referred to as "notch1 minimal decoy") may be particularly used.

Although the antagonist of DLL4 is possible to be bound to a N-terminal or C-terminal, or the like, of a heavy chain or a light chain of the antibody specifically bound to VEGFR-2 without limitation, preferably, may be bound to an N-terminal of the heavy chain or light chain, and more preferably, to an N-terminal of the light chain.

The most preferred dual-target antibody referred to as PMC-201 provided in the present invention has a form in which the antagonist of DLL4, in particular, the Notch1 minimal decoy to DLL4 is linked to the terminal, in particular, the N-terminal of the light chain, of the antibody specifically bound to VEGFR-2, wherein it is characterized in that the VEGFR-2-specific antibody is Tanibirumab and variants thereof.

The "angiogenesis" of the present invention means a cell phenomenon in which vascular endothelial cells are proliferated and reconstituted to form a new blood vessel from the existing blood vessel network. Angiogenesis factors promoting blood vessel generation, endothelial cell growth, blood vessel stability, and blood vessel formation are involved in the angiogenesis. The angiogenesis factors include members of vascular endothelial growth factor (VEGF) and VEGF family, placental growth factor (PlGF) family, platelet-derived growth factor (PDGF) family, DLL4, fibroblast growth factor family (FGF), TIE ligand (angiopoietin), ephrin, Del-1, fibroblast growth factor (acidic (aFGF) and basic (bFGF)), follistatin, granulocyte colony-stimulating factor (G-CSF), hepatocyte growth factor (HGF)/scatter factor (SF), interleukin-8 (IL-8), leptin, midkine, placental growth factor, platelet-derived endothelial cell growth factor (PD-ECGF), platelet-derived growth factor, in particular, PDGF-BB or PDGFR-beta, pleiotrophin (PTN), progranulin, proliferin, transforming growth factor-alpha (TGF-alpha), transforming growth factor-beta (TGF-beta), tumor necrosis factor-alpha (TNF-alpha), vascular endothelial growth factor (VEGF)/vascular permeation factor (VPF), and the like, but is not particularly limited thereto.

A term: "angiogenesis antagonist" of the present invention means a low-molecular weight material, polynucleotide, polypeptide, isolated protein, recombinant protein, antibody, or a conjugate therefor a dual-target antibody, which directly or indirectly inhibit blood vessel generation, blood vessel formation, or undesirable blood vessel permeability. In addition, the angiogenesis inhibitor includes a material which is bound to the angiogenesis factor or a receptor thereof to block the angiogenesis from being activated. For example, the angiogenesis inhibitor includes antibodies or other antagonists to angiogenesis agents such as VEGF-A or a soluble receptor of VEGF-A (for example, a soluble KDR receptor or a Flt-1 soluble receptor), VEGF-trap, angiopoietin 2, Notch1 soluble receptor decoy, or fragments maintaining a binding affinity to the ligands of the materials thereof, but the present invention is not limited thereto.

As described above, preferably, the present invention provides the dual-target antibody in a form in which the antagonist of DLL4, in particular, the Notch1 minimal decoy to DLL4 is connected to the terminal of the antibody specifically bound to VEGFR-2, wherein the VEGFR-2-specific antibody is preferably Tanibirumab or variants thereof, and preferably consists of a heavy chain variable region having any one sequence selected from SEQ ID NOS: 1 to 3 and a light chain variable region having any one sequence selected from SEQ ID NOS: 4 to 6.

Particularly, the VEGFR-2-specific antibody preferably consists of a heavy chain variable region of SEQ ID NO: 1 and a light chain variable region of SEQ ID NO: 4, a heavy chain variable region of SEQ ID NO: 2 and a light chain variable region of SEQ ID NO: 5, or a heavy chain variable region of SEQ ID NO: 3 and a light chain variable region of SEQ ID NO: 6, and the VEGFR-2-specific antibody may additionally include the constant region in the variable region. In addition, it is obvious to those skilled in the art that as long as the binding affinity to VEGFR-2 is possessed, fragments thereof or amino acid modification are also included in the scope of the present invention.

TABLE 1

Sequences of Hv and Lv of the antibody binding to VEGFR-2 according to the present invention

| SEQ ID NO. | Antibody | Sequences |
|---|---|---|
| 1 | Heavy chain Variable region | AQPAMAQMQL VQSGAEVKKP GASVKLSCKA SGYTFSSYWM HWVRQAPGQR LEWMGEINPG NGHTNYNEKF KSRVTITVDK SASTAYMELS SLRSEDTAVY YCAKIWGPSL TSPFDYWGQG TL |
| 2 | Heavy chain Variable region | QMQLVQSGAE VKKPGASVKL SCKASGYTFS SYWMHWVRQA PGQRLEWMGE INPGNGHTNY NEKFKSRVTI TVDKSASTAY MELSSLRSED TAVYYCAKIW GPSLTSPFDY WGQGTL |
| 3 | Heavy chain Variable region | QMQLVQSGAE VKKPGASVKL SCKASGYTFS SYWMHWVRQA PGQRLEWMGE INPGNGHTNY NEKFKSRVTI TVDKSASTAY MELSSLRSED TAVYYCAKIW GPSLTSPFDY WGQGTL |
| 4 | Light chain Variable region | SGVGSNFMLT QPPSVSVSPG KTARITCRGD NLGDVNVHWY QQRPGQAPVL VMYYDADRPS GIPERFSGSN SGNTATLTIS GVEAGDEADY YCQVWDRTSE YVFGTGTKVT VLG |
| 5 | Light chain Variable region | NFMLTQPPSV SVSPGKTARI TCRGDNLGDV NVHWYQQRPG QAPVLVMYYD ADRPSGIPER FSGSNSGNTA TLTISGVEAG DEADYYCQVW DRTSEYVFGT GTKVTVLG |
| 6 | Light chain Variable region | NFMLTQPPSV SVSPGKTARI TCRGDNLGDV NVHWYQQRPG QAPVLVMYYD ADRPSGIPER FSGSNSGNTA TLTISGVEAG DEADYYCQVW DRTSEYVFGT GTKVEIKRT |

In addition, Notch1 minimal decoy to DLL4 according to the present invention preferably consists of an amino acid sequence of SEQ ID NO: 7. However, it is also obvious to those skilled in the art that as long as an antagonism to DLL4 is maintained, variants having variations, deletion, and insertion of amino acids are also included in the scope of the present invention.

In the dual-target antibody according to the invention, the antibody which is specifically bound to VEGFR-2 and the antagonist of DLL4 may be liked with each other by various methods such as binding via a linker, chemically direct binding, genetic fusion, and the like. Preferably, the antibody and the antagonist may be linked by the binding via the linker, more preferably, by an amino acid linker. Preferable amino acid linker according to the present invention has an amino acid sequence of SEQ ID NO: 8.

TABLE 2

Amino acid sequences of Notch1 minimal decoy and amino acid linker according to the present invention

| SEQ ID NO. | Details | sequences |
|---|---|---|
| 7 | 11st and 12nd EGF-like domains of Notch1 receptor | DVDECSLGAN PCEHAGKCIN TLGSFECQCL QGYTGPRCEI DVNECVSNPC QNDATCLDQI GEFQCICMPG YEGVHCE |
| 8 | amino acid linker | SGGGGSGGGGSGS |

Therefore, a light chain-an amino acid linker-Notch1 minimal decoy protein of the dual-target antibody in which the Notch1 minimal decoy to DLL4 is linked to the light chain N-terminal of the dual-target antibody according to the present invention, via the amino acid linker has an amino acid sequence of SEQ ID NO: 9 or SEQ ID NO: 10.

TABLE 3

Amino acid sequences of a structure comprising light chain variable region of the dual-target antibody according to the present invention, in which Notch1 minimal decoy is bound thereto

| SEQ ID NO. | Sequences |
|---|---|
| 9 | DVDECSLGAN PCEHAGKCIN TLGSFECQCL QGYTGPRCEI DVNECVSNPC QNDATCLDQI GEFQCICMPG YEGVHCESGG GGSGGGGSGS NFMLTQPPSV SVSPGKTARI TCRGDNLGDV NVHWYQQRPG QAPVLVMYYD ADRPSGIPER FSGSNSGNTA TLTISGVEAG DEADYYCQVW DRTSEYVFGT GTKVTVLG |
| 10 | DVDECSLGAN PCEHAGKCIN TLGSFECQCL QGYTGPRCEI DVNECVSNPC QNDATCLDQI GEFQCICMPG YEGVHCESGG GGSGGGGSGS NFMLTQPPSV SVSPGKTARI TCRGDNLGDV NVHWYQQRPG QAPVLVMYYD ADRPSGIPER FSGSNSGNTA TLTISGVEAG DEADYYCQVW DRTSEYVFGT GTKVEIKRT |

(sequences of amino acid linker is underlined)

In addition, the present invention provides polynucleotide sequences encoding the dual-target antibody and a recombinant vector including the same.

The polynucleotide sequence encoding the dual-target antibody may be easily derived from the amino acid sequences of SEQ ID NOS: 1 to 10 by those skilled in the art. In addition, polynucleotide encoding leader sequence is allowed to be positioned at the N-terminal of the dual-target antibody, which is usable in production of the dual-target antibody according to the present invention.

A term: "recombinant vector" in the present invention is an expression vector capable of expressing a target protein in an appropriate host cell, and indicates a gene construct including essential controlling elements operably linked to each other so as to express gent inserts.

A term: "operably linked" in the present invention means that nucleic acid expression regulation sequences and nucleic acid sequences encoding target protein are functionally linked with each other so as to perform general functions. An operable link with the recombinant vector may be conducted by using gene recombinant technologies well known in the art, and site-specific DNA cleavage and linkage may be easily conducted by using enzymes generally known in the art.

Appropriate expression vectors of the present invention may include signal sequence for membrane targeting or secretion in addition to expression control elements such as a promoter, an initiation codon, a termination codon, polyadenylation signal and an enhancer. The initiation codon and the termination codon are generally considered as portions of nucleotide sequences encoding an immunological target protein, and when a gene construct is administered, function should be exhibited in an injected subject and should be in frame with coding sequences. A general promoter may be constitutive or inducible. Prokaryotic cells have lac, tac, T3 and T7 promoters, but the present invention is not limited thereto Eukaryotic cells have monkey virus 40 (SV40) promoter, mouse mammary tumor virus (MMTV) promoter, human immunodeficiency virus (HIV) promoter, for example, HIV long terminal repeats (LTR) promoter, moloney virus promoter, cytomegalovirus (CMV) promoter, epstein barr virus (EBV) promoter, rous sarcoma virus (RSV) promoter, and also have β-actin promoter, human hemoglobin-, human muscle creatine-, human metallothionein-derived promoters, but the present invention is not limited thereto.

The expression vector may include a selective marker for selecting a host cell containing a vector. The selective marker is to screen a cell transformed with the vector, wherein markers providing a selectable marker phenotype such as drug resistance, auxotrophy, resistance to a cytotoxic agent, or expression of a surface protein may be used Since only cells expressing the selectable marker are survive in environment treated with the selective agent, a transformed cell is possible to be selected. In addition, in the case in which the vector is a replicable expression vector, vector may include a replication origin which is a specific nucleic acid sequence initiating replication.

As a recombinant expression vector for inserting foreign genes, various vectors such as plasmid, virus, cosmid, and the like, may be used. The recombinant vector is not specifically limited in view of a kind as long as it expresses desired gene in various host cells of prokaryotic cells and eukaryotic cells, and produces desired protein; however, a vector capable of possessing strong expression with the promoter exhibiting strong activity while mass-producing the foreign protein in a form similar to a natural state is preferred.

In order to express the dual-target antibody according to the present invention, various expression host/vector combinations may be used. Examples of an expression vector which is appropriate for the eukaryotic host include expression regulatory sequences derived from SV40, bovine papilloma virus, adenovirus, adeno-associated virus, cytomegalovirus, and retro virus, but the present invention is not limited thereto. The expression vector usable in a bacterial host includes bacterial plasmids obtained from *escherichia coli*, such as pET, pRSET, pBluescript, pGEX2T, pUC vector, col E1, pCR1, pBR322, pMB9, and derivatives thereof, plasmid having a large range of host, such as RP4, phage DNA including significantly various phage lambda derivatives such as gt10, gt11, NM989, and other DNA phages such as M13 and filamentous single strand DNA phage. An expression vector useful for a yeast cell is 2 plasmid and derivatives thereof. A vector useful for an insect cell is pVL941.

According to another embodiment of the present invention, the present invention provides a host cell transformed with the recombinant vector. The recombinant vector is inserted into the host cell to form a transformant. Appropriate host cells of the vector may include a prokaryotic cell such as *Escherichia coli, Bacillus subtilis, Streptomyces* sp., *Pseudomonas* sp., *Proteus mirabilis* or *Staphylococcus* sp. In addition, the host cell may be an eukaryotic cell including fungi such as *Aspergillus* sp., yeast such as *Pichia pastoris, Saccharomyces cerevisiae, Schizosaccharomyces* sp. and *Neurospora crassa*, and other lower eukaryotic cells and higher eukaryotic cells from an insect. In addition, host cells may be derived from plants and mammals. Preferably, a monkey kidney cell 7 (COS7), an NSO cell, SP2/0, a chinese hamster ovary (CHO) cell, W138, a baby hamster kidney (BHK) cell, MDCK, myeloma cell line, HuT 78 cell and HEK293 cell, and the like, are available, but the present invention is not limited thereto. In particular, a CHO cell is preferred.

A term "transformation into a host cell" in the present invention may include any method in which nucleic acids are introduced into an organism, a cell, a tissue, or an organ, and may be performed by selecting appropriate standard technology depending on the host cell as known in the art. The method for transformation includes electroporation, protoplast fusion, calcium phosphate (CaPO$_4$) precipitation, calcium chloride (CaCl$_2$) deposition, stirring with silicon carbide fibers, *agrobacterium*-mediated transformation, polyethyleneglycol (PEG), polyethyleneimine (PEI), dextran sulfate, lipofectamine and dryness/inhibition-mediated transformation; however, the present invention is not limited thereto.

According to another embodiment of the present invention, the present invention provides a method of producing the dual-target antibody according to the present invention, including culturing host cells transformed with the recombinant vector.

The dual-target antibody according to the invention is preferably obtained by expression and purification by a gene recombinant method. Specifically, gene sequence encoding a heavy chain variable region or a heavy chain entire region of the antibody and gene sequence encoding a light chain variable region or a light chain entire region may be expressed in a single vector or in two vectors, separately, wherein the amino acid linker and/or gene sequence encoding the antagonist of DLL4 may be linked to a site corresponding to the N-terminal of the heavy chain or the light chain to induce expression in a cell expression system, thereby producing the dual-target antibody according to the present invention, but the present invention is not limited thereto.

Specifically, the method of producing the dual-target antibody may include: producing a recombinant vector by inserting nucleotide sequences encoding the dual-target antibody of the present invention into a vector; transforming the recombinant vector into a host cell and culturing the transformant; and isolating and purifying the dual-target antibody from the incubated transformant.

More specifically, the dual-target antibody may be mass-produced by culturing the transformant having expressed recombinant vector in a nutrient medium, wherein medium and incubation condition may be appropriately selected depending on a host cell. Conditions such as temperature, pH of medium, incubation time, and the like, may be appropriately controlled so as to be appropriate for growth and development of cells and mass-production of protein at the time of culturing.

Recombinantly-produced peptide or protein as described above may be recovered from medium or cell degradation. In the case of a membrane-coupled type, the peptide or the protein may be isolated from membrane by using an appropriate surfactant solution (for example: tritone-X 100) or enzymatic cleavage. Cells used in expression of the dual-target antibody may be destroyed by various physical or chemical means such as freeze-thaw purification, sonic treatment, mechanical damage and cell decomposing agent, and may be isolated and purified by general biochemical isolation technology (Sambrook et al., Molecular Cloning: A laboratory Manual, 2nd Ed., Cold Spring Harbor Laboratory Press (1989); Deuscher, M., Guide to Protein Purification Methods Enzymology, Vol. 182. Academic Press. Inc., San Diego, Calif. (1990)). Electrophoresis, centrifugation, gel filtration, precipitation, dialysis, chromatography (ion exchange chromatography, affinity chromatography, immunosorbent chromatography, size exclusion chromatography, and the like), isoelectric focusing, and various changes and complex methods are available, but the present invention is not limited thereto.

According to another embodiment of the present invention, the present invention provides a composition for inhibiting angiogenesis or treating cancer, the composition including the dual-target antibody. A term "anti-cancer" in the present invention includes "prevention" and "treatment"; wherein "prevention" means all behaviors in which cancer is inhibited or delayed by injection of the composition containing the antibodies of the present invention, and "treatment" means all behaviors in which symptoms of cancer are improved or changed in an advantageous way by the injection of the composition containing the antibodies of the present invention.

Cancers or tumors capable of being treated by the composition of the present invention are not particularly limited, but include solid tumor and blood cancer. Preferably, examples of cancer include colon cancer, colorectal cancer, gastric cancer, breast cancer, lung cancer, ovarian cancer, liver cancer, bronchial cancer, nasopharyngeal cancer, laryngeal cancer, pancreatic cancer, bladder cancer, pancreas cancer, cervical cancer, brain cancer, prostate cancer, bone cancer, skin cancer, thyroid cancer, parathyroid cancer, kidney cancer, esophageal cancer, biliary tract cancer, testis cancer, rectal cancer, head and neck cancer, cervical cancer, ureter cancer, osteosarcoma, neurocytoma, melanoma, fibrosarcoma, rhabdomyosarcoma, astrocytoma, neuroblastoma, neuroglioma, and the like.

The anti-cancer composition of the present invention may additionally include a pharmaceutically acceptable carrier. For oral administration, a binder, a lubricant, a disintegrant, an excipient, a solubilizer, a dispersant, a stabilizer, a suspending agent, pigment, flavouring, and the like, may be used. For an injection, a buffering agent, a preservative, a soothing agent, a solubilizing agent, an isotonic agent, a stabilizer may be mixed to be used. For topical administration, a basic substance, an excipient, a lubricant, a preservative, and the like, may be used. The pharmaceutical composition in the present invention may be mixed with the above-described pharmaceutically acceptable carrier to have various formulations. For example, for oral administration, the formulation may be formed as tablets, troches, capsules, elixir, suspension, syrup, wafer, and the like. For injection, the formulation may be prepared in a single unit dosage ampoule or in a multiple dosage form. In addition, the anti-cancer composition may typically include a surfactant facilitating movement including passage through membranes. Examples of the surfactant include materials derived from steroids, cationic lipids such as N-[1-(2,3-dioleoyl) propyl-N,N,N-trimethylammoniumchloride (DOTMA), various compounds such as cholesterol hemisuccinate, phosphatidyl glycerol, and the like.

According to another embodiment of the present invention, the present invention provides a method of treating cancer and inhibiting cancer growth by administering the dual-target antibody or the composition containing the dual-target antibody of the present invention to a subject. The composition containing the dual-target antibody according to the present invention may be administered in a pharmaceutically effective amount in order to treat cancer cell or metastasis thereof or to inhibit cancer growth. The administration amount may vary according to various factors such as cancer type, age and body weight of a patient, characteristics and severity of symptoms, kinds of current treatment, the number of treatments, administration type and route, and the like, and may be easily determined by experts in the corresponding art. The composition of the present invention may be administered together with the above-described pharmacological or physiological ingredients, or may be administered sequentially. In addition, the composition of the present invention may be administered in combination with additional conventional therapeutic agent, and may be administered sequentially or simultaneously with the conventional therapeutic agents. The administration may be a single or a multiple administration. It is important to administer an amount at which the maximum effect is obtained with a minimum amount without side effects in consideration of all of the above-described factors, and may be easily determined by those skilled in the art.

In the present invention, a term "subject" means a mammal suffering from a condition or disorder which is to be alleviated, inhibited or treated, or with such risk, by administering the dual-target antibody according to the present invention, preferably, a human.

In the present invention, a term "administration" means an introduction of a predetermined material to a subject by any appropriate method, wherein the composition containing the dual-target antibody of the present invention may be administered by any general route as long as the composition arrives at a desired tissue. Intraperitoneal administration, intravenous administration, intramuscular administration, subcutaneous administration, intradermal administration, oral administration, topical administration, intranasal administration, intrapulmonary administration, intrarectal administration may be used, but the present invention is not limited thereto. However, since protein is digested in the case of oral administration, an oral composition is preferred to be provided by coating an active agent thereon or to be formulated so as to protect the composition from being digested in the stomach. In addition, the pharmaceutical composition may be administered by any apparatus in which an active agent is movable to a target cell.

In addition, the present invention provides a method of measuring DLL4 antagonist efficacy of the dual-target antibody, the method including measuring Notch 1 activity by co-culture of a cell line expressing human DLL4 (hDLL4) or a recombinant cell line with human umbilical vein endothelial cells (HUVEC).

In the present invention, the Notch 1 activity is characterized by measuring an expression amount of NICD, and when the Notch ligand is bound to the Notch receptor, an ADAM metalloprotease is firstly activated to cleave a cellular membrane outer proximal site of the Notch receptor, and then a gamma-secretase complex is activated to cleave a cellular membrane inner proximal site of the Notch receptor, such that Notch Intracellular Domain (NICD) is isolated and migrates into the nucleus. NICD is bound to an RBPJ/CSL transcription factor to induce expression of Notch target genes such as basic helix-loop-helix proteins including Hes and Hey.

The measuring of the expression amount of NICD is performed by a method selected from the group consisting of SDS-PAGE, western blotting, immunohistochemical staining, immuno-staining, immunofluorescence, ELISA assay (direct measurements), and luciferase assay (indirect measurement), but may be performed by any known method for measuring protein expression in the art without limitation. In the present invention, the expression amount of NICD was preferably measured by western blotting.

Specifically, co-culture of the cell line expressing human DLL4 (hDLL4) or the recombinant cell line with HUVEC may be performed by including steps of (a) culturing HUVEC; and (b) reacting 293 cell line over expressing hDLL4 (293-hDLL4) and the dual-target antibody and performing treatment in the HUVEC cultured in the step (a) to achieve co-culture. It was confirmed that the expression amount of NICD exhibited by Notch-1 activation was reduced by the dual-target antibody PMC-201 by the co-culture method in Examples of the present invention.

In addition, according to the method for measuring hDLL4 antagonist efficacy of the dual-target antibody which is characterized in that Notch 1 activity is measured by the expression amount of NICD, NICD promoter activity may be measured with the NICD amount by using a luciferase assay method, and hDLL4 antagonist efficacy of the dual-target antibody may be measured by treating and culturing the HUVEC and the dual-target antibody PMC-201 in hDLL4-coated plates and measuring the NICD amount in the HUVEC, as confirmed in other Examples of the present invention.

Hereinafter, the present invention will be described in more detail with reference to the following Examples. However, the following examples are provided only for exemplifying the present invention, and it will be obvious to those skilled in the art that it is not construed to limit the scope of the present invention by these examples.

Example 1 Production of Expression Vector for Temporary Production of Dual-Target Antibody PMC-201

DNA encoding Notch1 minimal decoy (calcium-binding EGF-like domains 11 and 12 of a Notch1) bound to hDLL4 was obtained by gene synthesis (including gene optimization, GeneArt, Germany) after identifying amino acid base sequences (FIG. 1 and SEQ ID NO: 7) of corresponding domain.

77 amino acid base sequences were cloned to the light chain N-terminal of Tanibirumab (see TTAC0001 disclosed in International Patent Application No. PCT/KR07/003077) expression vector, by using a G4S linker (S GGGG SGGGGS GS) consisting of 13 amino acids to produce a dual-target antibody PMC-201 expression vector with optimized expression in 293-T cell line (ATCC, CRL-11268™) (FIG. 2). The confirmed recombinant vector was named as 'PMC-201-v213'.

Example 2: Production and Identification of Dual-Target Antibody PMC-201

Random expression of the completed expression vector PMC-201-v213 into a 293T cell by transduction was induced, and occurrence of the expression was confirmed by SDS-PAGE and western blotting. The transduction was used by Lipofectamine™ 2000 (Invitrogen #11668-019, U.S.A), and was followed by instruction of the manufacturer. Briefly, $5 \times 10^5$ per well of 293T cells were inoculated into 6-well plates containing αMEM medium (Welgene, Republic of Korea), and then allowed to stand in $CO_2$ (5%) humidified incubator at 37° C. for 24 hours, thereby achieving dense culturing having a cell density of about 80% to 90%. 2 µg of the recombinant vector (PMC-201-v213) and 6 µl of Lipofectamin™ 2000 were diluted in 250 µl of serum-free αMEM mediums, respectively, and left at room temperature for 5 minutes.

A DNA dilution solution was mixed with Lipofectamin™ 2000 dilution solution and allowed to react at room temperature for 20 minutes, to form DNA-Lipofectamin™ 2000 complex. After existing medium was removed from the incubated cell, 500 µl of DNA-Lipofectamin™ 2000 complex and 500 µl of serum-free αMEM medium were added to each well, and incubated in a $CO_2$ incubator at 37° C. for 6 hours. 1 ml αMEM medium containing 20% dialyzed fetal calf serum was added thereto and incubated for 48-72 hours. Then, only the supernatant was separated, and whether or not the antibody was expressed was confirmed by SDS-PAGE. SDS-PAGE was performed by methods known in the art, and samples were used as follows: 12% SDS-polyacrylamide Gel, PVDF membrane (Millipore #IPVH00010, U.S.A.), HRP-conjugated goat anti-human IgG (kappa) antibody, and HRP-conjugated goat anti-human IgG (Fc) antibody (Pierce, U.S.A.).

Figure 3:
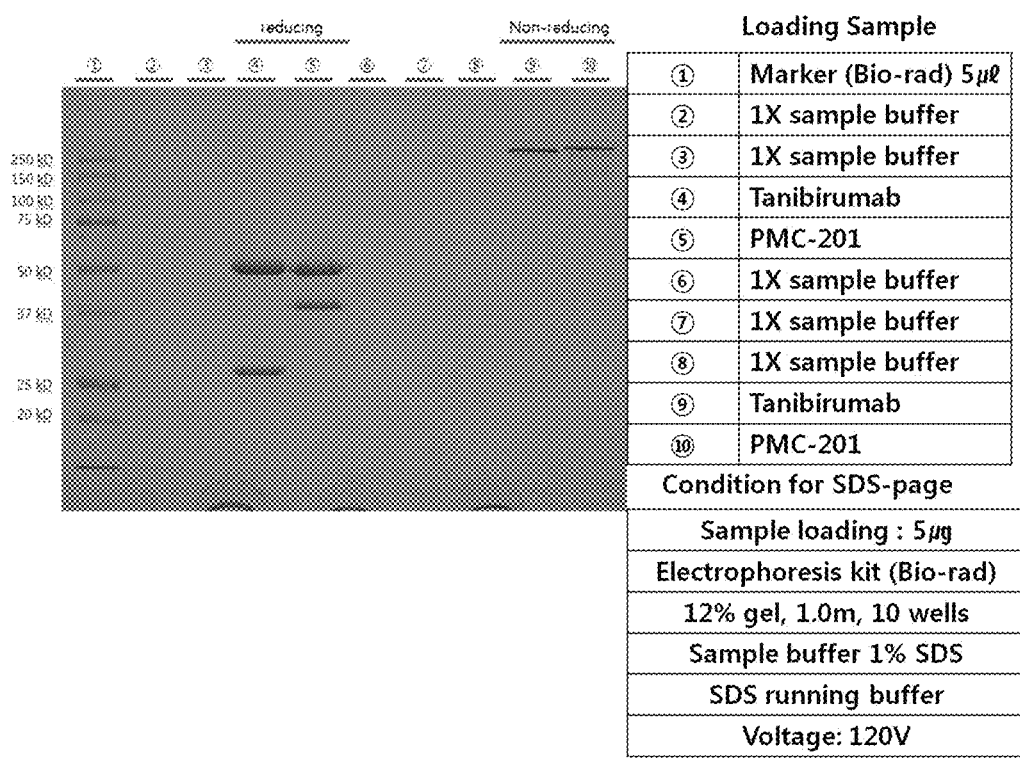
FIG. 3 represents results obtained by randomly expressing the vector according to the present invention by using a 293-T cell and confirming production of a purified dual-target antibody through SDS-PAGE.

As a result, it was confirmed that the dual-target antibody PMC-201 was expressed by SDS-PAGE and western blotting, and purified antibodies having purity of 95% or more were obtained by Fast protein liquid chromatography (FPLC) using Protein A affinity column, SP-sepharose column, and size exclusion column (FIG. 3).

Example 3: Binding Affinity Test of Dual-Target Antibody PMC-201

3-1: Binding Affinity Test to VEGFR-2 and hDLL4

A binding affinity assay confirming whether or not the dual-target antibody PMC-201 was bound to VEGFR-2 and hDLL4 was performed by using ELISA. 1 μg/ml of extracellular domains 1 to 3 of VEGFR-2 (hereinafter, referred to as VEGFR-2 ECD) and DLL4 were each divided and coated in a 96-well plate at room temperature for 2 hours, and a blocking reaction was performed at room temperature for 2 hours, using 2% skim milk/PBS.

After the plates after the blocking was finished was washed with PBS, previously prepared Tanibirumab and PMC-201 at various concentrations (0.18 to 3000 ng/ml) at room temperature were added to wells coated with VEGFR-2 ECD or hDLL4, and allowed to react at room temperature for 1 hour. After the reaction was finished, the product was washed with PBS, and then 1:2000 dilution of HRP-conjugated goat anti-human IgG antibody (Pierce, U.S.A.) was added as a secondary antibody and reacted at room temperature for 30 minutes. A colorimetric reaction was induced by TMB substrate reagent (BD Biosciences #555214, U.S.A.) and was stopped by adding 50 μl of 2N sulfuric acid ($H_2SO_4$) solution. Measurement of the colorimetric reaction was performed at absorbance of 450 nm and 650 nm by using a microplate reader (Tecan, Switzerland).

Figure 4:
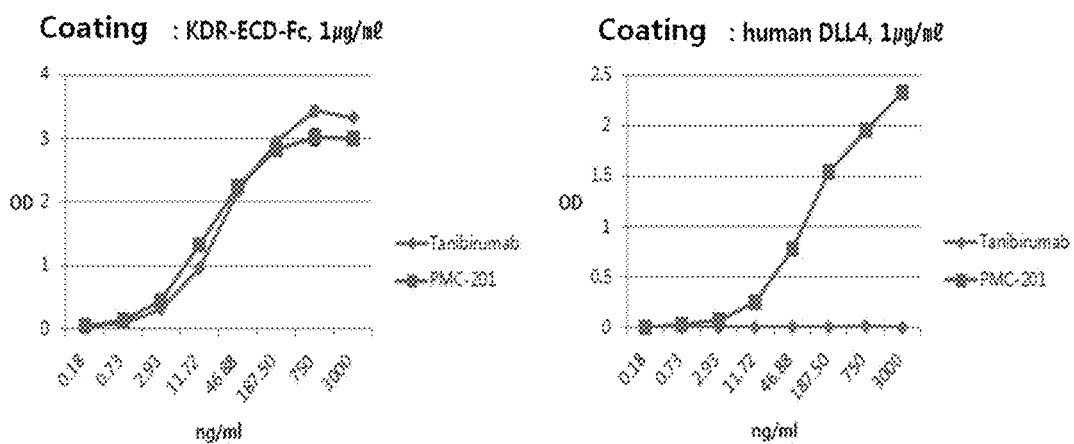
FIG. 4 represents ELISA-analysis results of binding affinity to VEGFR-2 and human DLL4, of the dual-target antibody according to the present invention.

As a result, it was confirmed that Tanibirumab and PMC-201 had similar binding affinity in VEGFR-2; however, it was confirmed that only the PMC-201 had a binding affinity in hDLL4 (FIG. 4).

3-2: Affinity Analysis of PMC-201 and Human DLL4

In order to calculate Kd (dissociation constant) of PMC-201 to human DLL4, BIACORE® 3000 (GE Healthcare) was used, and CM5 chip was used. The dissociation constant is similar to Km value, and is used as an affinity index of an enzyme to a substrate in an enzyme-substrate complex. The affinity between the enzyme and the substrate is increased as the dissociation constant is decreased.

The sample was immobilized by using 400 mM EDC (N-ethyl-N'-(dimethylaminopropyl) Carbodiimide), 100 mM NHS (N-Hydroxysuccinimide), and 1 M ethanolamine hydrochloride (pH 8.5) that are an Amine Coupling Kit (GE Healthcare), and 20 mM sodium hydroxide as a generation buffer, and 1×PBS as an immobilization buffer were diluted, and then the analysis sample was 1:40 diluted in 10 mM acetate (pH 5.0) (GE Healthcare). The sample was immobilized at 4000RU (Response Unit). A buffer for measuring adsorption of the analysis sample was a HBS-EP buffer (GE Healthcare). DLL4s having measurement concentrations of 4.9, 9.7, 19.5, 39.1, 78.1, 156.3, 312.5 nM as an antigen were serial-diluted so as to have a final volume of 200 μl by using an HBS-EP buffer. Five concentrations of seven concentrations were selected and fitted. A concentration of the used generation buffer was selected by confirmation with about 10% higher than a base line by using sodium hydroxide, after the sample (156.3 nM) was subjected to a binding step and a dissociation step for preliminary experiment before actual analysis. Affinity of the analysis sample was measured under conditions in which an analysis flow rate was 30 μl/min, a binding section was 60 seconds, and a dissociation was 300 seconds.

Figures 5, 6:
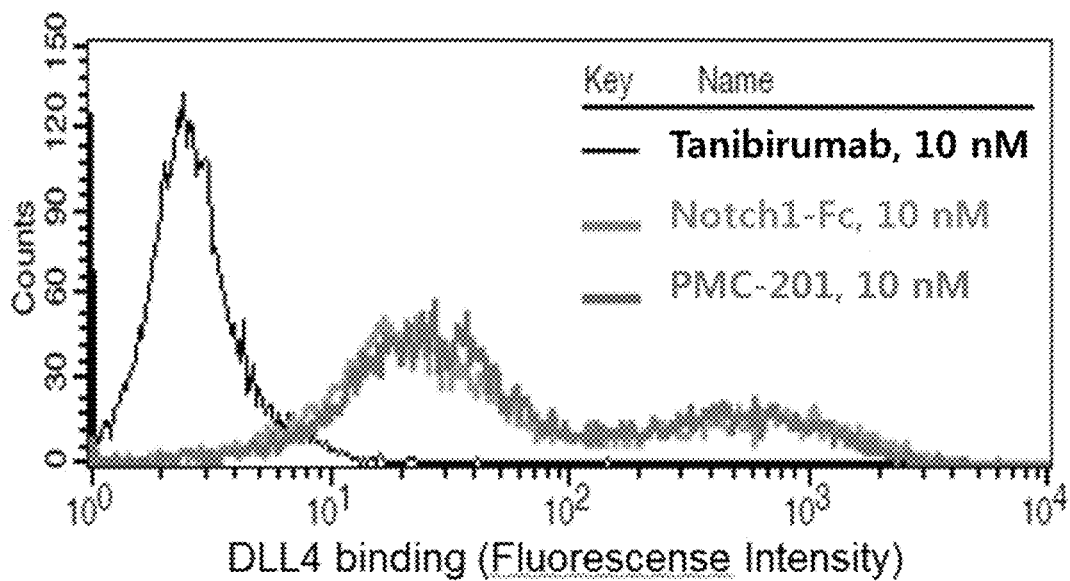
FIG. 5 represents Biacore-analysis results of binding affinity to human DLL4, of the dual-target antibody according to the present invention.
FIG. 6 represents Flow cytometer-analysis results of binding affinity to human DLL4, of the dual-target antibody according to the present invention.

As the analysis result of the affinity for each batch, each affinity was confirmed in PMC-201 and Notch-1 Fc, and the dual-target antibody PMC-201 of the present invention had higher affinity as compared to Notch-1 Fc (FIG. 5).

3-3: Measurement of Binding Affinity of hDLL4 and PMC-201 Expressed on Cell Surface ELISA and Biacore were used to measure binding affinity of PMC-201 to hDLL4 immobilized in a solid-phase, and FACS analysis was performed to confirm whether or not PMC-201 was bound to hDLL4 expressed on the cell surface (FIG. 6).

First, in order to produce 293 pool and a cell line expressing hDLL4 (SEQ ID NO: 12 amino acid sequence), coding sequence of hDLL4 (SEQ ID NO: 11 sequence) in which gene optimization was performed was cloned at restriction enzyme BamHI and EcoRI positions of pcDNA3.1 (+) by Geneoptimizer of GeneArt to construct pcDNA-hDLL4. Then, the pcDNA-hDLL4 vector was transduced into 293 cells. The transduction was used by using Lipofectamine™ 2000 (Invitrogen #11668-019, U.S.A), and was followed by instruction of the manufacturer. Briefly, $1 \times 10^6$ of 293 cells were inoculated into 100 mm well plates containing αMEM medium (Welgene, Republic of Korea), and then incubated in $CO_2$ (5%) humidified incubator at 37° C. for 24 hours so as to have cell density of about 20%. 16 μg of vector (DLL4 pcDNA3.1) and 40 pt of Lipofectamin™ 2000 were diluted in 1 ml of serum-free αMEM medium and incubated at room temperature for 5 minutes, and then DNA dilution solution was mixed with Lipofectamin™ 2000 dilution solution, and reacted at room temperature for 20 minutes to form a DNA-Lipofectamin™ 2000 complex. After the existing medium was removed from the incubated cells, 1 me of DNA-Lipofectamin™ 2000 complex and 9 me of serum-free αMEM medium were added to each well, and incubated in a $CO_2$ humidified incubator at 37° C. for 6 hours, then, the medium was replaced with a DMEM medium containing 10% dialyzed fetal calf serum. Then, the medium was incubated at 37° C. for 72 hours, cells were separated by Trypsin-EDTA, and then, DMEM medium containing 10% dialyzed fetal calf serum and neomycin (G418, 500 μg/ml) were added and incubated. After 72 hours, the medium was replaced with a medium of which G418 concentration was increased by 1 mg/ml, and incubated under the same condition for about 1 week until colonies were formed. Each colony was treated with Trypsine-EDTA in plates having colonies formed therein, and was moved to a 24-well plate. DMEM medium containing 10% dialyzed fetal calf serum and neomycin (G418, 500 μg/ml) were added and incubated, and all growing colonies were collected and incubated in a pool state.

After 1 week, FACS analysis was performed with anti-hDLL4 antibody (Biolegend, U.S.A.) in a pool state to confirm hDLL4 expression, and 23 kinds of single colonies were selected and subincubated in 6-well plate and 100 mm plate, respectively and incubated in DMEM medium containing 10% dialyzed fetal calf serum and neomycin (G418, 500 μg/ml). One kind of cell favorably expressing hDLL4 was selected among single colonies, and named as 293-hDLL4, and used for DLL4 antagonist efficacy-related analysis of PMC-201.

FACS analysis was conducted in order to confirm that PMC-201 was favorably bound to 293-DLL4 pool. First, a sufficient number ($1 \times 10^6$ or more per FACS sample) of 293-DLL4 pool was incubated, and made as single cell with Trypsin-EDTA, and 2 ml of 1×FACS buffer (0.2% BSA in PBS) was added and mixed well, followed by centrifugation at 1200 rpm for 3 minutes. A supernatant was discarded and cells at the bottom were primarily stained with 10 nM concentration of PMC-201, Notch-1 Fc, and Tanibirumab with ice for 20 minutes, washed with 1×FACS buffer, and were secondarily stained (20 minutes in ice) with PE-anti-human Fc antibody and washed. Then, flow cytometry; FACSCalibur was used for measurement.

As a result obtained by measuring whether or not PMC-201 was bound to hDLL4 expressed on cell surface, it was confirmed that PMC-201 had similar binding affinity to Notch-1 Fc (FIG. 6).

Example 4: Analysis of HUVEC Proliferation Ability after Treatment of Dual-Target Antibody PMC-201

Cell proliferation ability analysis was performed to confirm change in proliferation ability of Human umbilical vein endothelial cell (HUVEC) (Lonza, Switzerland), after treatment of the dual-target antibody PMC-201 according to the present invention. HUVEC was incubated by using phenol red-free M199 medium (Invitrogen, U.S.A.) containing 20% fetal calf serum (Hyclone, U.S.A.), 100 units/m, of penicillin (Hyclone, U.S.A.), 100 μg/ml of streptomycin (Hyclone, U.S.A.), 3 ng/ml of fibroblast growth factor (Upstate Biotechnology, U.S.A.) 5 units/me of heparin (Sigma-Aldrich, U.S.A.), in an incubator at 37° C. with 5% $CO_2$ humidified mixed air. These cells were incubated in 24-well plates at density of $2 \times 10^4$ cell/well for 24 hours in order to analyze survival rate of HUVEC. Then, cells were washed with M199 medium twice, and incubated under a low serum concentration condition in M199 medium containing 1% fetal calf serum (Hyclone, U.S.A.) for 6 hours. Various concentrations of antibodies were pre-treated in cells for 30 minutes, and treated with 20 ng/me VEGF (R&D systems, U.S.A.). After incubation for 48 hours, cells were treated with WST-8 (Dojindo, Japan) for 2 hours, absorbance at 450 nm wavelength was measured, and cell proliferation ability under each condition was compared to each other.

Figure 7:
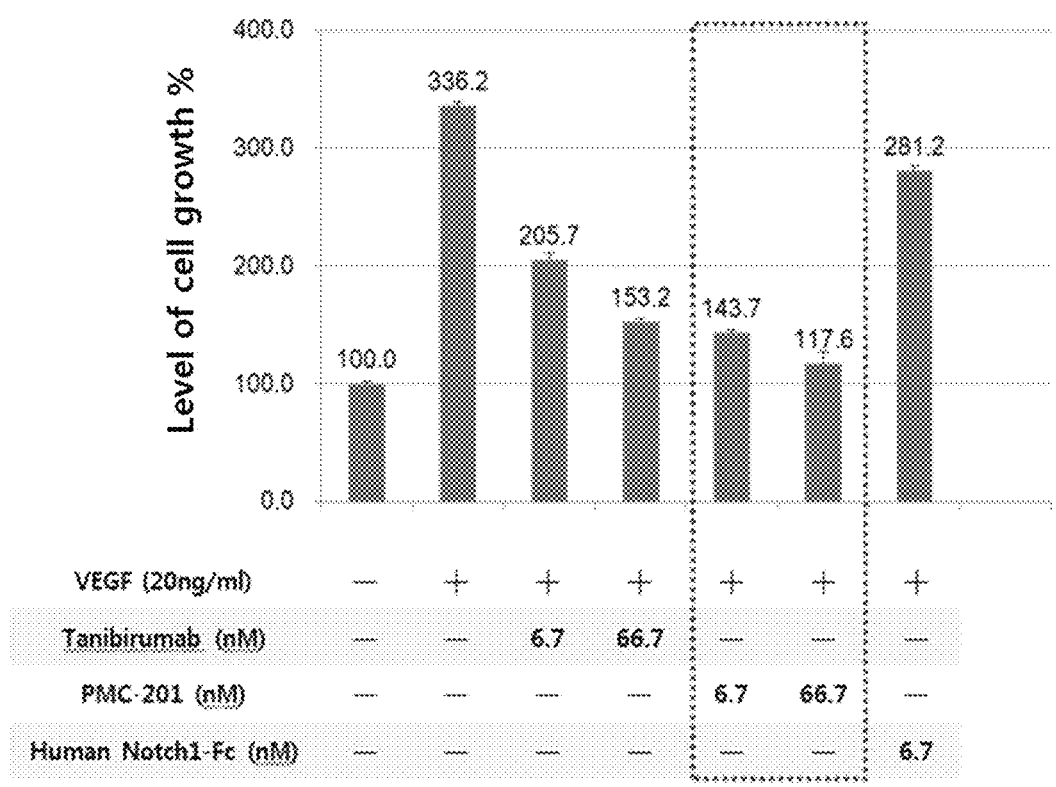
FIG. 7 represents proliferation assay results on HUVEC, of the dual-target antibody according to the present invention.

As a result, it was confirmed from cell proliferation ability assay on initially incubated HUVEC that dual-target antibody PMC-201 could more strongly inhibit proliferation ability of HUVEC induced by VEGF as compared to the parent antibody Tanibirumab (FIG. 7).

Example 5: Analysis of Competitive Human DLL4 Binding Affinity Using FACS

FACS analysis was performed to confirm whether or not PMC-201 was competitively bound to hNotch1-Fc bound to 293-hDLL4 cell line. First, a sufficient number ($1 \times 10^6$ or more of cells per FACS sample) of 293-hDLL4 were incubated and treated with Trypsin-EDTA to be isolated into single cells, and then, 2 ml of 1×FACS buffer (0.2% BSA in PBS) was added. Then, isolated single cells were recovered and centrifuged at 1,200 rpm for 3 minutes, and then supernatant was discarded. 16 μg/ml of Tanibirumab or PMC-201 and 1 μg/ml of rhNotch1-Fc having labeled Alexa-488 (Zenon, #Z-25402) were added to the cells at the bottom, primarily stained in ice for 30 minutes, washed with 1×FACS buffer, and measured by flow cytometry (FACSCalibur).

Figure 8:
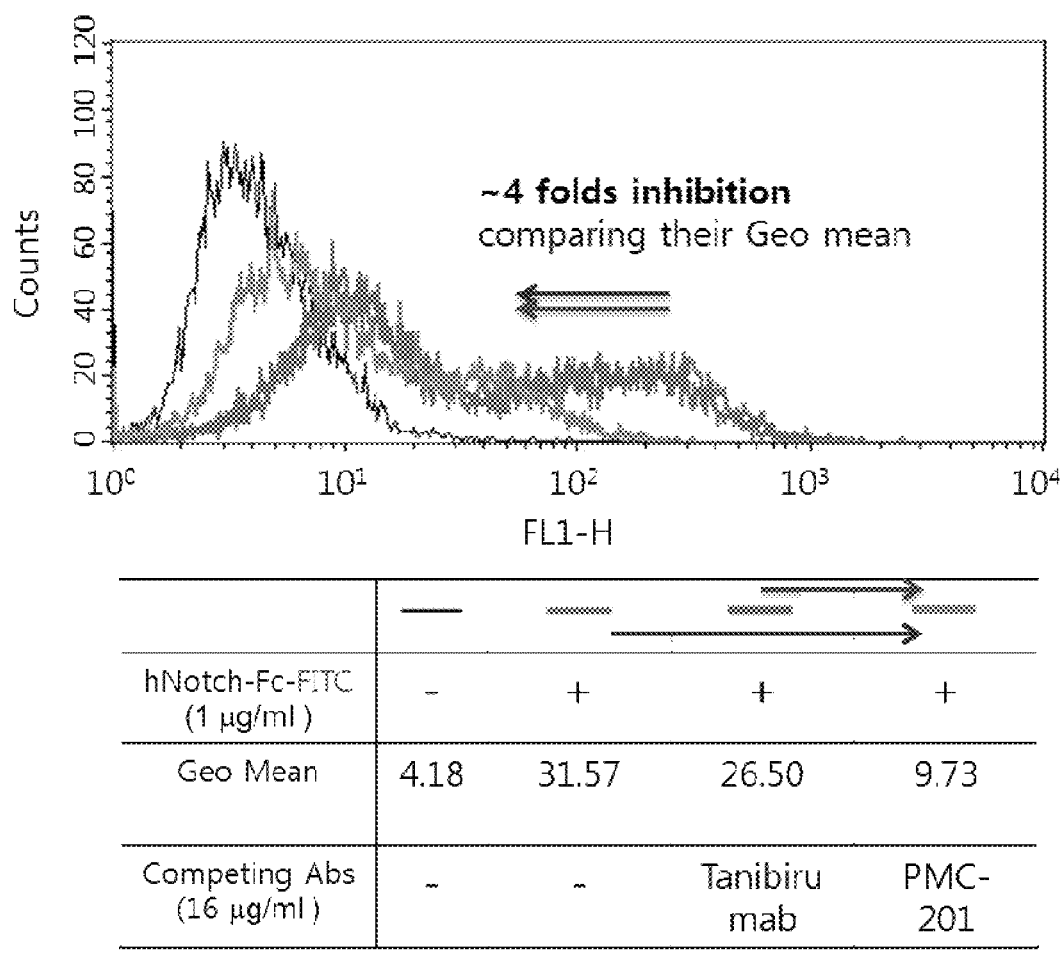
FIG. 8 represents FACS-analysis results of phenomenon that the dual-target antibody according to the present invention competitively suppresses binding of Notch-Fc to human DLL4.

As a result, it was confirmed that the binding of rhNotch1-Fc bound to the HUVEC was four-times decreased in consideration of Geometric mean by PMC-201. Meanwhile, Tanibirumab could not inhibit the binding of rhNotch1-Fc antibody, which is similar to an untreated antibody group (FIG. 8).

Example 6 Analysis of Promoter Activity by Notch-1

$1 \times 10^5$ LS174T cells (colon cancer cell line; ATCC, CL-188™) were incubated in RPMI medium containing 10% of fetal calf serum for 24 hours, and 0.8 μg of Notch Cignal reporter DNA contained in Cignal Reporter Assay Kit (#336841 CCS-014L, QIAGEN) and 2 μl of lipofectamine (#11668-500; Invitrogen) were mixed with 100 μl of opti-MEM media and allowed to stand for 20 minutes, and then 400 μl of opti-MEM was added for transfection to incubate cells for 6 hours. After 6 hours, the medium was replaced with an MEM medium containing 10% fetal calf serum, and incubated overnight. Next day, Tanibirumab and PMC-201 (each of 20 mg/ml) were mixed and pre-treated in $1 \times 10^5$ of 293-hDLL4 cells for 1 hour, then co-cultured with LS174T cells transfected with Notch Cignal reporter DNA for 24 hours. DAPT (5 mM) was not pre-treated and 293-hDLL4 cell was mixed with the transfected LS174T cells, and co-cultured for 24 hours.

DAPT N—[N-(3,5-Difluorophenacetyl)-L-alanyl]-S-phenylglycine t-butyl ester) is generally known to inhibit Notch 1 activity, and inhibit activity of γ-secretase to decrease an increase in NICD production (Andrea Geling et al., *EMBO Rep.,* :3(7):688, 2002; Ie-Ming Shih and Tian-Li Wang, *Cancer Research,* 67:1879, 2007).

After co-culture for 24 hours, cells were lyzed by using a lysis buffer contained in Dual-Luciferase Reporter Assay System (Cat.#E1910; Promega), and a substrate and ATP were mixed with each other, and then luminescence amount was measured by using Luminometer.

Figure 9:
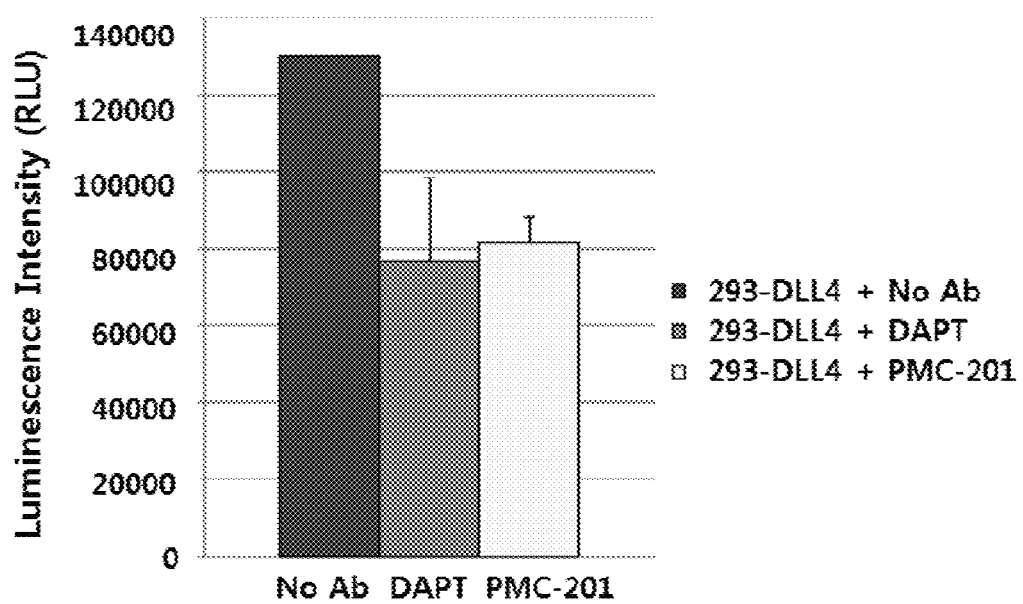
FIG. 9 represents luciferase luminescence assay results of phenomenon that the dual-target antibody according to the present invention suppresses promoter activation by Notch-1.

As a result, it was confirmed that promoter activation of NICD exhibited by Notch-1 activation of LS174T cells was decreased in cells treated with the dual-target antibody PMC-201, similar to DAPT treatment groups, as compared to Comparative Group having untreated antibody (FIG. 9).

Example 7: Analysis of Increase in Notch Intracellular Domain (NICD) by Activation of Notch-1

1 μg/ml concentration of recombinant hDLL4 was coated with 6-well plate overnight (16 hours), and washed with 1×PBS. Human IgG (hIgG), Tanibirumab, PMC-201 (20 μg/ml) were treated in each well for 1 hour, and treated antibody solutions were removed. $5 \times 10^5$ of HUVEC and IgG, Tanibirumab, PMC-201 (20 μg/ml) were mixed with each other and treated in 6-well plates, respectively. After 24 hours incubation, cells were lyzed by using a lysis buffer (final 1% SDS, 1 mM Na3VO4, lx protease inhibitor cocktail), and cell solution was collected and transferred to an Eppendorf tube, and heated at 95° C. for 10 minutes and cooled in ice. Total protein was quantified by using BCA quantification method, and NICD was measured by the same method as Western blotting of Example 2.

Here, a primary antibody was 1:1000 dilution of Cleaved Notch1 (Val1744) (D3B8) antibody (Rabbit), β-actin antibody (Rabbit) was 1:2000 dilution in skim milk containing 5% 0.05% TBST, and a secondary antibody was 1:1000 dilution of anti-Rabbit IgG (R&D HAF008).

Figure 10:
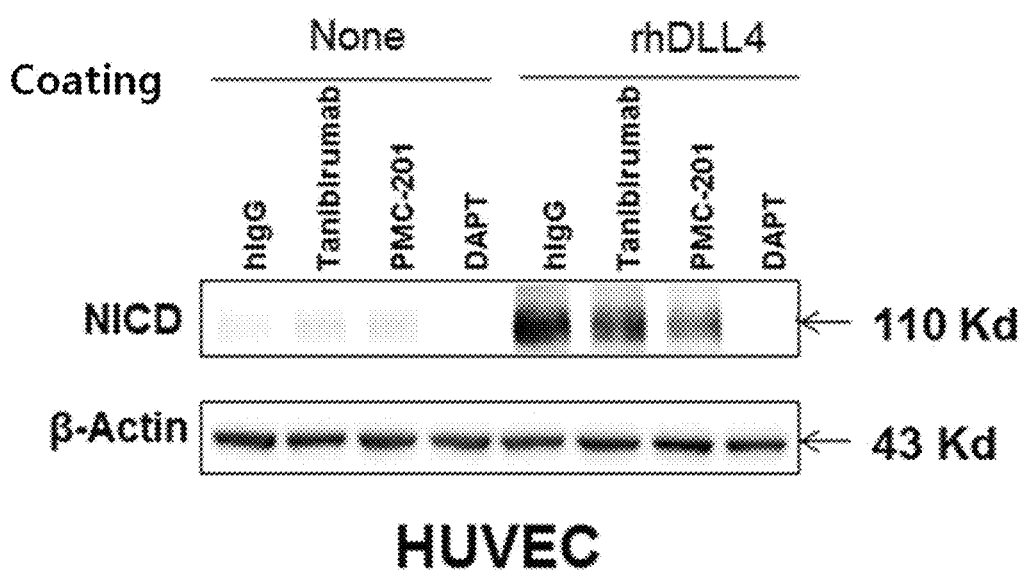
FIG. 10 represents western blotting-analysis results of phenomenon that an increase in notch intracellular domain (NICD) by activation of Notch-1 is suppressed, at the time of culturing the dual-target antibody according to the present invention and HUVEC in a culture dish coated with hDLL4.

As a result, it was confirmed that an amount of NICD exhibited by hNotch-1 activation in the HUVEC cell was significantly decreased by the dual-target antibody PMC-201 targeting DLL4 as compared to Tanibirumab which is a parent antibody (FIG. 10).

Meanwhile, an analysis method of detecting NICD only by cell culture and co-culture without coating hDLL4 was performed as follows.

First, $5 \times 10^5$ cell/well of HUVEC was incubated in 6-well plate for 24 hours. Then, $2.5 \times 10^5$ cell/well of 293-hDLL4 (human DLL4 over-expression 293 cell line) and hIgG, PMC-201 (10 μg/ml) DAPT (5 uM) were treated for 1 hour, and antibodies (hIgG, PMC-201) and 293-hDLL4 cells treated with DAPT were added to initially incubated HUVEC in 6-well plates, without removing the antibody solution, and co-cultured for 24 hours. As a comparative group, 293-T cell line was treated and co-cultured with HUVEC.

After co-culture for 24 hours, the cells were lyzed by using a lysis buffer (final 1% SDS, 1 mM Na3VO4, 1x protease inhibitor cocktail), and cell solution was collected and transferred to an Eppendorf tube, and heated at 95° C. for 10 minutes and cooled in ice. Total protein was quantified by using BCA quantification method, and NICD was measured by the same method as Western blotting of Example 2.

Figure 11:
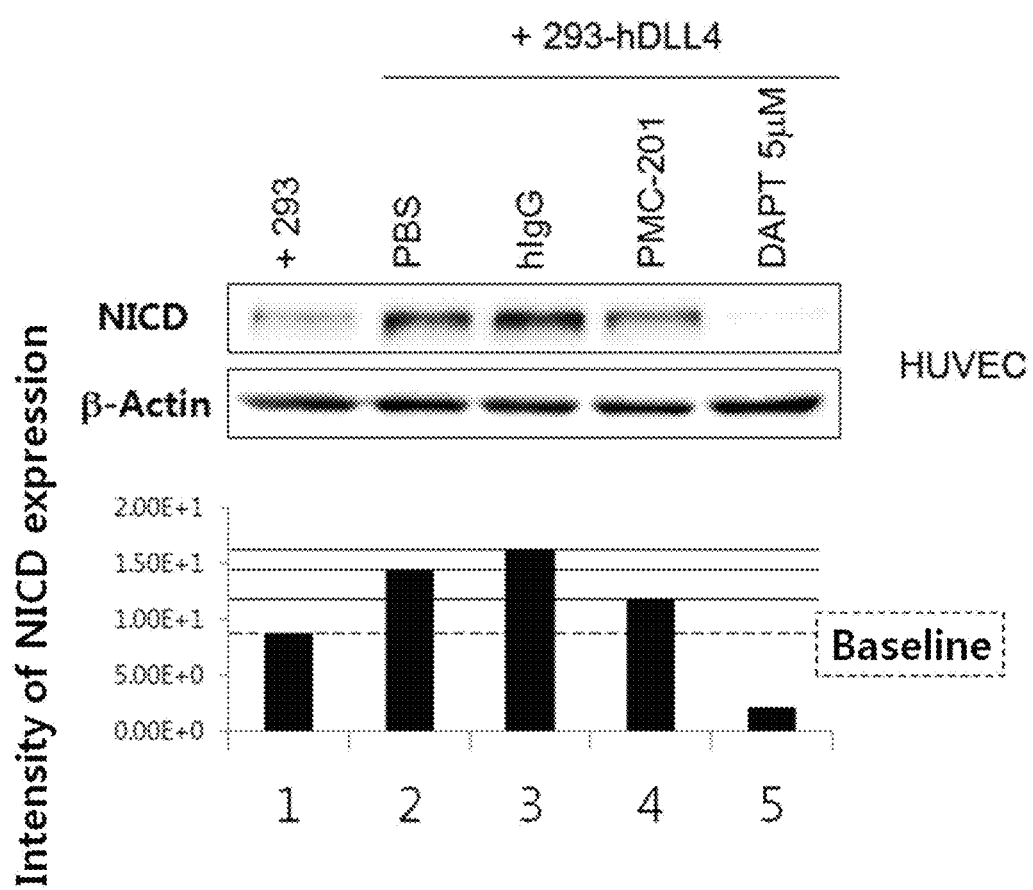
FIG. 11 represents western blotting-analysis results of phenomenon that an increase in notch intracellular domain (NICD) by activation of Notch-1 is suppressed, at the time of co-culturing the dual-target antibody according to the present invention and HUVEC in a 293 cell line expressing hDLL4.

As a result, it was confirmed that an amount of NICD exhibited by Notch-1 activation in the HUVEC cell was decreased to be less than 50% by the dual-target antibody PMC-201 targeting DLL4 as compared to hIgG (FIG. 11).

INDUSTRIAL APPLICABILITY

The dual-target antibody according to the present invention may more effectively and simultaneously inhibit signaling of two paths, VEGF/VEGFR-2 and DLL4/Notch1, thereby treating various angiogenesis-related diseases such as tumor, and the like, and particularly, overcoming resistance caused by using a neovascular therapeutic agent alone, and fundamentally preventing recurrence of cancer by directly targeting cancer stem cells.

Therefore, the dual-target antibody according to the present invention and the pharmaceutical composition including the same may be effectively used for treatment of angiogenesis-related diseases, particularly, cancer.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A dual-target antagonist targeting VEGFR-2 and DLL4, comprising DLL4 antagonist, which is bound to a terminal of antibody binding to VEGFR-2,
wherein the DLL4 antagonist is 11$^{th}$ and 12$^{th}$ calcium-binding EGF-like domains of human Notch1, and the amino acid sequence of said domains is SEQ ID NO: 7; and
the DLL4 antagonist is bound to the N-terminal of light chain variable region of the antibody binding to VEGFR-2.

2. The dual-target antagonist according to claim 1, wherein the antibody binding to VEGFR-2 is Tanibirumab or variants thereof.

3. The dual-target antagonist according to claim 1, wherein the DLL4 antagonist is bound to the antibody binding to VEGFR-2 via amino acid linker.

4. The dual-target antagonist according to claim 1, wherein the antibody binding to VEGFR-2 comprises a heavy chain variable region comprising the amino acid sequence of SEQ ID NO: 1 and a light chain variable region comprising the amino acid sequence of SEQ ID NO: 4;
a heavy chain variable region comprising the amino acid sequence of SEQ ID NO: 2 and a light chain variable region comprising the amino acid sequence of SEQ ID NO: 5; or
a heavy chain variable region comprising the amino acid sequence of SEQ ID NO: 3 and a light chain variable region comprising the amino acid sequence of SEQ ID NO: 6.

* * * * *

UNITED STATES PATENT AND TRADEMARK OFFICE
CERTIFICATE OF CORRECTION

| | |
|---|---|
| PATENT NO. | : 9,963,512 B2 |
| APPLICATION NO. | : 14/443617 |
| DATED | : May 8, 2018 |
| INVENTOR(S) | : Joong Kyu Kim |

Page 1 of 1

It is certified that error appears in the above-identified patent and that said Letters Patent is hereby corrected as shown below:

Column 3, Line 14: "WO02008/153237" should be -- WO2008/153237 --.

Signed and Sealed this
Third Day of July, 2018

Andrei Iancu
*Director of the United States Patent and Trademark Office*